United States Patent [19]

King et al.

[11] 4,034,107

[45] July 5, 1977

[54] SUBSTITUTED (ALKOXYCARBONYLTHIOUREIDO)-(ACYLAMINO)-BENZENE DERIVATIVES

[75] Inventors: Leslie George King, London; Glyn Evan Lee, Thorpe Bay; George Christopher James Martin, Brentwood; David Conwil Jenkins, Barkingside, all of England

[73] Assignee: May and Baker Limited, Dagenham, England

[22] Filed: Nov. 4, 1975

[21] Appl. No.: 628,669

[30] Foreign Application Priority Data

Nov. 5, 1974 United Kingdom ............ 47889/74

[52] U.S. Cl. ............................. 424/309; 260/470; 260/252; 260/253; 260/505 R; 424/253; 424/315

[51] Int. Cl.² ............... A61K 31/24; C07C 149/40; A01N 9/20

[58] Field of Search .......... 260/470, 471, 252, 253, 260/505; 424/315, 253, 300, 309

[56] References Cited

UNITED STATES PATENTS 3,843,715 10/1974 Widdig et al. .................... 260/470

*Primary Examiner*—Sam Rosen
*Attorney, Agent, or Firm*—Stevens, Davis, Miller & Mosher

[57] ABSTRACT

Benzene derivatives of the formula:

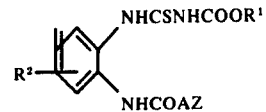

wherein $R^1$ represents alkyl, $R^2$ represents a group $-SR^3$, $-SOR^3$, $-SO_2R^3$, $-OR^3$, $-SCONH_2$, $-SCN$ or $-T(CH_2)_mT^1R^4$ [wherein $R^3$ represeents alkyl, cycloalkyl, alkenyl, alkynyl, aralkyl, unsubstituted or substituted aryl, or cycloalkylalkyl, $R^4$ represents hydrogen or alkyl, T and $T^1$ each represent oxygen, sulphur or sulphinyl, and $m$ is an integer from 1 to 7] whose position on the benzene ring is either para to the group $-NHCSNHCOOR^1$ or para to the group $-NHCOAZ$, A represents a bivalent straight-chain aliphatic hydrocarbon radical of 1 to 4 carbon atoms or a said hydrocarbon radical substituted by at least one methyl group, and Z represents a group of the formula:-

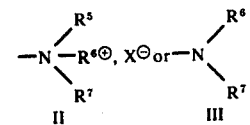

wherein $R^5$ represents hydrogen or alkyl, $R^6$ represents hydrogen, alkyl or phenylalkyl, and $R^7$ represents hydrogen or alkyl, or $R^6$ and $R^7$ together with the nitrogen atom to which they are attached form a 5-,6- or 7-membered heterocyclic ring optionally substituted by alkyl group(s), and $X^-$ represents a pharmaceutically acceptable anion, are new compounds useful as anthelmintics and antifungal agents.

53 Claims, No Drawings

SUBSTITUTED (ALKOXYCARBONYLTHIOUREIDO)-(ACYLAMINO)-BENZENE DERIVATIVES

This invention relates to benzene derivatives, compositions containing them and their use as anthelmintics and antifungal agents.

As a result of research and experimentation, it has now been found that the new benzene derivatives of the general formula:

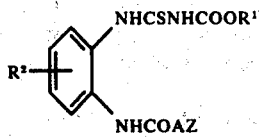

wherein $R^1$ represents a straight- or branched-chain alkyl group containing not more than 4 carbon atoms (preferably methyl), $R^2$ represents a group of the formula $-SR^3$, $-SOR^3$, $-SO_2R^3$, $-OR^3$, $-SCONH_2$, $-SCN$ or $-T(CH_2)_mT^1R^4$ [wherein $R^3$ represents a straight- or branched-chain alkyl group containing not more than 6 carbon atoms, e.g. methyl or ethyl, a cycloalkyl group containing from 3 to 7 carbon atoms, e.g. cyclopentyl, a straight- or branched-chain alkenyl or alkynyl group containing from 3 to 6 carbon atoms, e.g. allyl or prop-2-ynyl, an aralkyl, e.g., phenylalkyl, group with 1 or 2 carbon atoms in the alkyl moiety, for example benzyl, or $R^3$ represents an aryl, e.g., phenyl, group which may optionally be substituted by a halogen (e.g. chlorine) atom or by a stright- or branched-chain alkyl or alkoxy group containing from 1 to 3 carbon atoms, or represents a cycloalkylalkyl group in which the cycloalkyl moiety contains from 3 to 7 carbon atoms and the alkyl moiety contains 1 to 2 carbon atoms, e.g. cyclohexylmethyl, $R^4$ represents a hydrogen atom or, preferably, a straight- or branched-chain alkyl group containing not more than 4 carbon atoms, e.g. ethyl, T and $T^1$, which may be the same or different, each represent an oxygen or sulphur atom or a sulphinyl ($-SO-$) group, and m is an integer from 1 to 7 inclusive and is preferably 2] whose position on the benzene ring is either para to the group $-NHCSNHCOOR^1$ or para to the group $-NHCOAZ$, A represents a bivalent straight chain aliphatic hydrocarbon radical containing not more than 4 carbon atoms which may be saturated or unsaturated (e.g. a methylene, polymethylene e.g. ethylene, or vinylene radical) and which may optionally be substituted by at least one methyl group, and Z represents a group of the general formula:

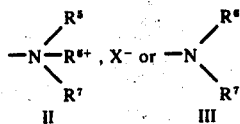

wherein $R^5$ represents a hydrogen atom or a straight- or branched-chain alkyl group containing not more than 4 carbon atoms, e.g. methyl or ethyl, $R^6$ represents a hydrogen atom or a straight- or branched-chain alkyl group containing not more than 4 carbon atoms, e.g. methyl or ethyl, or a phenylalkyl group with 1 or 2 carbon atoms in the alkyl moiety, preferably benzyl, and $R^7$ represents a hydrogen atom or a straight- or branched-chain alkyl group containing not more than 4 carbon atoms, e.g. methyl or ethyl, or $R^6$ and $R^7$ together with the nitrogen atom to which they are attached form a 5-, 6- or 7-membered heterocyclic ring which may contain in the ring one or two further hetero atoms selected from oxygen, nitrogen and sulphur, and which may optionally be substituted by one or more straight- or branched-chain alkyl groups each containing not more than 6 carbon atoms, for example a pyrrolidin-1-yl, piperidino, morpholino, piperazin-1-yl or 4-alkylpiperazin-1-yl, e.g. 4-methylpiperazin-1-yl, group and $X^-$ represents a pharmaceutically acceptable or agriculturally acceptable anion, possess valuable chemotherapeutic properties, having, in particular, high anthelmintic and anti-fungal activity.

When the compounds of general formula I can exist in stereoisomeric forms, all such isomers and their mixtures and racemates are included within the scope of the present invention.

The term 'pharmaceutically acceptable anion' means an anion which is relatively innocuous to the animal organism when used in therapeutic doses so that the beneficial properties of the cation are not vititated by side-effects ascribable to the anion.

The term 'agriculturally acceptable anion' means an anion which is generally regarded as acceptable for use in agricultural practice, being relatively innocuous to the vegetable organism when used at fungicidal rates of application, so that the beneficial properties of the cation are not vitiated by side-effects ascribable to that anion.

Good examples of anions within the definition of $X^-$ are halide ions (e.g. chloride, bromide and iodide ions) and the methanesulphonate, sulphate, nitrate, phosphate, acetate, citrate, propionate, succinate, benzoate, fumarate, maleate, tartrate, theophyllinacetate, salicylate, phenolphthalinate, methylene-bis-$\beta$-hydroxynaphthoate, amsonate and isethionate ions.

According to a feature of the present invention, there is provided a method for the treatment of helminth infections in man and domestic animals, for example cattle, sheep, pigs, goats, poultry and equines, for example infections of the gastro-intestinal tract caused by parasitic nematode worms, for example members of the family Trichostrongylidae, and infections by parasitic trematodes of the genus Fasciola (e.g. *Fasciola hepatica*, otherwise known as liver flukes) in domestic animals, which comprises the administration of an anthelmintically effective amount of one or more compounds of general formula I.

The quantities of the compounds of formula I administered in the treatment of helminthiasis will vary with the species of animal treated, the nature and severity of the infection, the length of treatment and the method of administration. In general, the compounds are effective in treating helminthiasis when administered to domestic animals in dosages which may be as low as 1 mg/kg of animal body weight but which are preferably from about 4 mg/kg to about 50 mg/kg of animal body weight. Higher doses up to 250 mg/kg of animal body weight may, however, be used.

The quantities referred to above of the compounds of general formula I may be administered on one or more occasions or divided into a number of smaller doses and administered over a period.

The value of the compounds of formula I as anthelmintics has, for example, been demonstrated in the following tests.

In Tables I and V hereafter the form in which the test compounds were administered are shown in the columns headed "Form", in which the symbols have the following meanings:

"B" means that the free base was used (i.e. a compound wherein Z represents a group of formula III), "C" means that the hydrochloride salt was used (i.e. a compound wherein Z represents a group of formula II wherein $R^5$ represents a hydrogen ion and $X^-$ represents a chloride ion), and "M" means that the methanesulphonate salt was used (i.e. a compound wherein Z represents a group of formula II wherein $R^5$ represents a hydrogen ion and $X^-$ represents a methanesulphonate ion).

Where it is indicated that a methanesulphonate salt was administered but where that particular methanesulphonate salt is not specifically described in the following preparative Examples, the methanesulphonate salt was prepared by treatment of the free base with aqueous methanesulphonic acid solution (0.2N) in equimolecular proportions, followed by dilution with water to a convenient volume for administration.

A. Activity against roundworms in rats

Test 1 - Rats were infected with 100 *Nippostrongylus brasiliensis* larvae each, by the subcutaneous route. After 6 days, when the infection was patent, the rats were randomised and allotted to groups of 5 animals each, ready for treatment. One group was used for each dose level of the test compound, which was administered by the oral or subcutaneous route and, in each experiment, one group of 10 animals was left untreated as a control. All the rats were killed for post-mortem worm counts 48 hours after treatment.

The activities, expressed in terms of the percentage reduction in mean worm load of the treated groups compared with the untreated group, are shown in Table I.

Test 2 - Rats were infected with 100 *Nippostrongylus brasiliensis* larvae each, by the subcutaneous route. After 24 hours the rats were randomised and allotted to groups of 5 animals each, ready for treatment. Doses of the test compound were then administered to each group by the oral or subcutaneous route, one group of 10 animals being left untreated as a control. All the rats were killed for post-mortem worm counts 6 days after dosing. The activities, expressed in terms of the percentage reduction in mean worm load of the treated groups compared with the untreated control group, are given below in Table I.

Test 3 - Rats were infected with 100 *Nippostrongylus brasiliensis* larvae, each by the subcutaneous route. After 24 hours the hair on the rats' backs was clipped, taking care to avoid skin damage, and the rats were randomised and allotted to groups of 5 animals each, ready for treatment. The animals were anaesthetised. A 10% w/v solution of the test compound in dimethyl sulphoxide was applied topically to the clipped area of each animal in the group, one group of 10 animals being left untreated as a control. Dimethyl sulphoxide solvent was also applied topically to the clipped area of each animal in a separate group of 5 animals. All the rats were killed for post-mortem worm counts 6 days after treatment. The activities, expressed in terms of the percentage reduction in mean worm load of the treated groups compared with the untreated control group, are given below in Table II.

In the Tables "sc" stands for "subcutaneous".

TABLE I

| Test Compound | Test | Form | Dose mg/kg animal body weight | Route of Administration | Percentage reduction in N. brasiliensis load |
|---|---|---|---|---|---|
| 4-(3-methoxycarbonyl-2-thioureido)-3-(2-dimethyl-aminoacetamido)diphenyl thioether | 1 | B | 100 | oral | 100 |
| | 1 | M | 100 | sc | 31 |
| | 2 | B | 250 | oral | 100 |
| | 2 | B | 100 | oral | 100 |
| | 2 | B | 25 | oral | 99 |
| | 2 | M | 25 | sc | 99 |
| 3-(3-methoxycarbonyl-2-thioureido)-4-(2-dimethyl-aminoacetamido)diphenyl thioether | 1 | C | 100 | oral | 99 |
| | 1 | M | 100 | sc | 36 |
| | 2 | C | 25 | oral | 99 |
| | 2 | M | 25 | sc | 88 |
| 4-(2-aminoacetamido)-3-(3-methoxycarbonyl-2-thioureido)diphenyl thioether | 1 | B | 50 | oral | 97 |
| | 1 | M | 50 | sc | 96 |
| | 2 | B | 12.5 | oral | 99 |
| | 2 | M | 12.5 | sc | 99 |
| 4-(2-aminoacetamido)-3-(3-ethoxycarbonyl-2-thioureido)diphenyl thioether | 2 | B | 50 | oral | 95 |
| 3-(3-methoxycarbonyl-2-thioureido)-4-[2-(N-methyl-amino)acetamido]diphenyl thioether | 2 | B | 12.5 | oral | 99 |
| | 2 | M | 25 | sc | 99 |
| | 2 | M | 12.5 | sc | 96 |
| | 1 | B | 100 | oral | 97 |
| 3-(2-aminoacetamido)-4-(3-methoxycarbonyl-2-thioureido)diphenyl thioether | 1 | B | 100 | oral | 99 |
| | 1 | M | 100 | sc | 54 |
| | 2 | B | 50 | oral | 99 |
| | 2 | M | 50 | sc | 99 |
| 4-(2-aminoacetamido)-3-(3-methoxycarbonyl-2-thioureido)-4'-methyl diphenyl thioether | 1 | B | 100 | oral | 84 |
| | 1 | M | 100 | sc | 62 |
| | 2 | B | 25 | oral | 95 |
| | 2 | M | 50 | sc | 94 |
| 4'-chloro-3-(3-methoxycarbonyl-2-thioureido)-4-(2-dimethylamino-acetamido)diphenyl thioether | 1 | B | 100 | oral | 92 |
| | 2 | B | 50 | oral | 99 |
| | 2 | M | 50 | sc | 94 |
| 3-(2-aminoacetamido)-4-(3-methoxycarbonyl-2-thioureido)diphenyl ether | 1 | B | 100 | oral | 90 |
| | 1 | M | 100 | sc | 34 |
| | 2 | B | 50 | oral | 97 |
| | 2 | M | 50 | sc | 98 |
| 4-(3-methoxycarbonyl-2- | 2 | C | 100 | oral | 97 |

TABLE I-continued

| Test Compound | Test | Form | Dose mg/kg animal body weight | Route of Administration | Percentage reduction in N. brasiliensis load |
|---|---|---|---|---|---|
| thioureido)-3-(2-dimethyl-aminoacetamido)diphenyl ether | 2 | C | 100 | sc | 61 |
| 3-(3-methoxycarbonyl-2-thioureido)-4'-methyl-4-(2-dimethylamino-acetamido)diphenyl thioether | 1 | B | 100 | oral | 56 |
|  | 2 | B | 100 | oral | 97 |
|  | 2 | M | 100 | sc | 51 |
| 4-(2-aminoacetamido)-4'-chloro-3-(3-methoxy-carbonyl-2-thioureido)-diphenyl thioether | 1 | B | 100 | oral | 98 |
|  | 1 | M | 100 | sc | 75 |
|  | 2 | B | 50 | oral | 100 |
|  | 2 | M | 100 | sc | 99 |
| 4-(3-methoxycarbonyl-2-thioureido)-3-(2-pyrrolidin-1-ylacetamido)-diphenyl thioether | 1 | B | 100 | oral | 98 |
|  | 2 | B | 25 | oral | 99 |
|  | 2 | M | 25 | sc | 78 |
| 2-(3-ethoxycarbonyl-2-thioureido)-1-(2-dimethyl-aminoacetamido)-4-methyl-sulphonylbenzene | 1 | C | 100 | oral | 61 |
|  | 2 | C | 100 | oral | 96 |
|  | 2 | C | 250 | sc | 92 |
| 4-(3-methoxycarbonyl-2-thioureido)-3-(3-dimethylaminopropionamido)-diphenyl thioether | 1 | B | 100 | oral | 50 |
|  | 2 | B | 50 | oral | 99 |
|  | 2 | M | 50 | sc | 95 |
| 3-(2-diethylamino-acetamido)-4-(3-methoxy-carbonyl-2-thioureido)-diphenyl thioether | 1 | B | 100 | oral | 99 |
|  | 2 | B | 25 | oral | 98 |
|  | 2 | M | 25 | sc | 98 |
| 1-(3-methoxycarbonyl-2-thioureido)-3-(2-dimethyl-aminoacetamido)-4-methylthiobenzene | 2 | B | 100 | oral | 87 |
|  | 2 | M | 100 | sc | 97 |
| 4-(3-methoxycarbonyl-2-thioureido)-3-(2-dimethyl-aminoacetamido)diphenyl-sulphoxide | 1 | C | 100 | oral | 99 |
|  | 2 | C | 50 | oral | 100 |
| 4-allylthio-1-(3-methoxy-carbonyl-2-thioureido)-2-(2-dimethylaminoacetamido)-benzene | 1 | B | 100 | oral | 81 |
|  | 1 | M | 100 | sc | 44 |
|  | 2 | B | 50 | oral | 97 |
|  | 2 | M | 50 | sc | 97 |
| 3-(2-diethylamino-acetamido)-4-(3-methoxy-carbonyl-2-thioureido)-diphenyl ether | 1 | C | 100 | oral | 65 |
|  | 2 | C | 50 | oral | 94 |
|  | 2 | C | 100 | sc | 97 |
| 4-benzylthio-1-(3-methoxy-carbonyl-2-thioureido)-2-(2-dimethylaminoacetamido)-benzene | 1 | B | 100 | oral | 93 |
|  | 1 | M | 100 | sc | 70 |
|  | 2 | B | 50 | oral | 98 |
|  | 2 | M | 50 | sc | 95 |
| 4-ethylthio-1-(3-methoxy-carbonyl-2-thioureido)-2-(2-dimethylaminoacetamido)-benzene | 1 | B | 100 | oral | 86 |
|  | 2 | B | 50 | oral | 92 |
|  | 2 | M | 50 | sc | 92 |
| 4-n-butylthio-1-(3-methoxycarbonyl-2-thio-ureido)-2-(2-dimethyl-aminoacetamido)-benzene | 1 | B | 100 | oral | 88 |
|  | 1 | M | 100 | sc | 48 |
|  | 2 | B | 50 | oral | 97 |
|  | 2 | M | 50 | sc | 93 |
| 4-(3-methoxycarbonyl-2-thioureido)-3-(2-dimethyl-aminopropionamido)diphenyl thioether | 1 | B | 100 | oral | 100 |
|  | 2 | B | 12.5 | oral | 95 |
|  | 2 | M | 25 | sc | 95 |
| 4-cyclopentylthio-1-(3-methoxycarbonyl-2-thio-ureido)-2-(2-dimethyl-aminoacetamido)benzene | 2 | B | 50 | oral | 93 |
|  | 2 | M | 100 | sc | 90 |
| 4-(2-ethylthioethylthio)-1-(3-methoxycarbonyl-2-thioureido)-2-(2-dimethyl-aminoacetamido)benzene | 2 | B | 100 | oral | 92 |
|  | 2 | M | 100 | sc | 69 |

TABLE II

| Test Compound | Dose mg/kg animal body weight | Percentage reduction in N. brasiliensis worm load |
|---|---|---|
| 4-(3-methoxycarbonyl-2-thoureido)-3-(2-dimethylaminoacetamido)-diphenylthioether | 200 | 99 |
| 4-(3-methoxycarbonyl-2-thioureido)-3-(2-dmethylaminoacetamido)-diphenylthioether methane-sulphonate | 200 | 99 |
| dimethyl sulphoxide solvent | 2000 | 0 |

B. In vitro activity against roundworms

Compounds of formula I were tested at concentrations of 100μg/ml, 10μg/ml, 1μg/ml and a0.1μg/ml in small glass containers. If the compound was not soluble in water, a volatile organic medium, e.g. acetone, chloroform, ethanol or methanol was used. An amount of material appropriate for each final concentration was measured and placed in duplicate test containers and if an organic solvent was used it was allowed to evaporate completely.

*Nippostrongylus brasiliensis* eggs were recovered by saturated saline centrifugal flotation from the faeces of rats heavily infected with third stage larvae six days previously. They were washed several times in water and suspended in water in a suitable concentration. From 25–50 eggs were placed in each container and the final volume was made up by the addition of a very dilute aqueous suspension of mouse faeces which served as the growth medium.

The minimum inhibitory concentrations of each compound (M.I.C.), shown in the following Table III was the minimum concentration in μg/ml total liquid volume at which it inhibited or delayed hatching of eggs, or at which it killed, retarded growth or reduced activity of larvae during the 4 days after beginning the test.

TABLE III

| Compound | M.I.C. (μg/ml) |
| --- | --- |
| 4-(3-methoxycarbonyl-2-thioureido)-3-(2-dimethylaminoacetamido)diphenyl thioether | 0.1 |
| 3-(3-methoxycarbonyl-2-thioureido)-4-(2-dimethylaminoacetamido)diphenyl thioether hydrochloride | 0.1 |
| 4-(2-aminoacetamido)-3-(3-methoxycarbonyl-2-thioureido)diphenyl thioether | 0.1 |
| 4-(3-methoxycarbonyl-2-thioureido)-3-(2-trimethylammonioacetylamino)diphenyl thioether iodide | 0.1 |
| 4-(2-aminoacetamido)-3-(3-ethoxycarbonyl-2-thioureido)diphenyl thioether | 0.1 |
| 3-(2-aminoacetamido)-4-(3-methoxycarbonyl-2-thioureido)diphenyl thioether | 100 |
| 4-(2-aminoacetamido)-3-(3-methoxycarbonyl-2-thioureido)-4'-methyldiphenyl thioether | 0.1 |
| 4'-chloro-3-(3-methoxycarbonyl-2-thioureido)-4-(2-dimethylaminoacetamido)diphenyl thioether | 0.1 |
| 3-(2-aminoacetamido)-4-(3-methoxycarbonyl-2-thioureido)diphenyl ether | 0.1 |
| 4-(3-methoxycarbonyl-2-thioureido)-3-(2-dimethylaminoacetamido)diphenyl ether hydrochloride | 0.1 |
| 3-(3-methoxycarbonyl-2-thioureido)-4'-methyl 4-(2-dimethylaminoacetamido)diphenyl thioether | 0.1 |
| 4-(2-aminoacetamido)-4'-chloro-3-(3-methoxycarbonyl-2-thioureido)diphenyl thioether | 0.1 |
| 4-(3-methoxycarbonyl-2-thioureido)-3-(2-pyrrolidin-1-ylacetamido)diphenyl thioether | 0.1 |
| 4-(3-methoxycarbonyl-2-thioureido)-3-(2-morpholin-4-ylacetamido)diphenyl thioether | 0.1 |
| 4-(3-methoxycarbonyl-2-thioureido)-3-(3-dimethylaminopropionamido)diphenyl thioether | 0.1 |
| 3-(2-diethylaminoacetamido)-4-(3-methoxycarbonyl-2-thioureido)diphenyl thioether | 0.1 |
| 1-(3-methoxycarbonyl-2-thioureido)-2-(2-dimethylaminoacetamido)-4-methylthiobenzene | 1.0 |
| 4-(3-n-butoxycarbonyl-2-thioureido)-2-(2-dimethyl aminoacetamido)diphenyl thioether | 0.1 |
| 4-allylthio-1-(3-methoxycarbonyl-2-thioureido)-2-(2-dimethylaminoacetamido)benzene | 0.1 |
| 3-(2-dimethylaminoacetamido)-4-[3-(2-methylpropoxycarbonyl)-2-thioureido]diphenyl thioether | 10.0 |
| 3-(2-diethylaminoacetamido)-4-(3-methoxycarbonyl-2-thioureido)diphenyl ether hydrochloride | 0.1 |
| 4-benzylthio-1-(3-methoxycarbonyl-2-thioureido)-2-(2-dimethylaminoacetamido)benzene | 0.1 |

TABLE III-continued

| Compound | M.I.C. (μg/ml) |
| --- | --- |
| 4-ethylthio-1-(3-methoxycarbonyl-2-thioureido)-2-(2-dimethylaminoacetamido)benzene | 0.1 |
| 4-n-butylthio-1-(3-methoxycarbonyl-2-thioureido-2-(2-dimethylaminoacetamido)benzene | 0.1 |
| 4-(3-methoxycarbonyl-2-thioureido)-3-(2-dimethyl-aminopropionamido)diphenyl thioether | 0.1 |
| 4-cyclopentylthio-1-(3-methoxycarbonyl-2-thioureido)-2-(2-dimethylaminoacetamido)benzene | 0.1 |

C. Activity against roundworms in sheep a. Activity against *Haemonchus contortus* and *Nematodirus spathiger* in their adult stages in lambs.

Worm-free, 8–10 week old lambs were each infected with 5000 *H. contortus* and 15000 *N. spathiger* larvae. Approximately 3 weeks later, doses of the test compound were administered to each group of 2 animals, either by the oral or the subcutaneous route, one group of 2 animals being left untreated as a control.

Individual faecal *H. contortus* egg counts were determined 1 day before and 5–7 days after treatment, when all the lambs were killed for post-mortem worm counts. The activities, expressed in terms of the percentage reduction in mean worm burden of each worm species compared with the untreated control group, are given below in Table IV.

b. Activity against *Haemonchus contortus*, *Ostertagis circumcincta*, *Trichostrongylus axei*, *Trichostronglyus colubriformis* and *Nematodirus spathiger* in their 4th larval and adult stages in lambs.

Worm-free, 8–10 week old lambs were each infected with 5,000 *H. contortus*, 15,000 *O. circumcincta*, 20,000 *T. axei*, 15,000 *T. colubriformis* and 15,000 *N. Spathiger* larvae.

Doses of the test compound were then administered to each group of 2 animals, either by the oral, or the subcutaneous or the intramuscular route after 7 days or 21 days to examine the effects against the 4th larval stage and mature adult worms respectively, one group of 2 animals being left untreated as a control. All the lambs were killed for post-mortem worm counts 24 days after infection. The activities, expressed in terms of the percentage reduction in mean worm burden of each worm species compared with the untreated control group, are given below in Table V. In Table V the test compounds are 4-(3-methoxycarbonyl-2-thioureido)-3-(2-dimethylamino-acetamido)diphenyl thioether (P), 4-(3-methoxycarbonyl-2-thioureido)-3-(2-dimethylamino-acetamido)diphenyl thioether (Q), 4-(2-aminoacetamido)-3-(3-methoxycarbonyl)-2-thioureido)-diphenyl thioether (R), 4-(3-methoxycarbonyl-2-thioureido)-3-(2-dimethylamino-acetamido)diphenyl ether (S), 3-(2-diethylaminoacetamido)-4-(3-methoxycarbonyl-2-thioureido)diphenyl thioether (T) and 4-(3-methoxycarbonyl-2-thioureido)-3-(3-dimethylamino)-propionamido)diphenyl thioether (U).

TABLE IV

| Test Compound | Dose mg/kg animal body weight | Route of Administration | Percentage reduction in mean worm burdens | |
|---|---|---|---|---|
| | | | H. contortus | N. spathiger |
| 4-(3-methoxycarbonyl 2-thioureido)-3-(2-dimethyl-aminoacetamido)diphenyl thioether | 10<br>5 | oral<br>oral | 100<br>100 | 100<br>87 |
| 4-(3-methoxycarbonyl-2-thioureido)-3-(2-dimethyl-aminoacetamido)diphenyl thioether methanesulphonate | 25<br>10 | sc<br>sc | 100<br>100 | 100<br>54 |
| 3-(3-methoxycarbonyl-2-thioureido)-4-(2-dimethyl-aminoacetamido)diphenyl thioether hydrochloride | 10 | oral | 100 | 86 |
| 3-(3-methoxycarbonyl-2-thioureido)-4-(2-dimethyl-aminoacetamido)diphenyl thioether methanesulphonate | 10 | sc | 100 | 63 |
| 4-(2-aminoacetamido)-3-(3-methoxycarbonyl-2-thioureido)-diphenyl thioether | 10 | oral | 100 | 80 |
| 4-(2-aminoacetamido)-3-(3-methoxycarbonyl-2-thio-ureido)diphenyl thioether methanesulphonate | 10 | sc | 100 | 51 |
| 4-(2-aminoacetamido)-3-(3-ethoxycarbonyl-2-thioureido)diphenyl thioether | 10 | oral | 100 | 44 |
| 4-(2-aminoacetamido)-3-(3-ethoxycarbonyl-2-thioureido)diphenyl thioether methanesulphonate | 10 | sc | 98 | 40 |
| 3-(3-methoxycarbonyl-2-thioureido-4-[2-(N-methyl-amino)acetamido]diphenyl thioether methanesulphonate | 10 | sc | 100 | 50 |
| 3-(2-aminoacetamido)-4-(3-methoxycarbonyl-2-thioureido)diphenyl thioether methanesulphonate | 10 | sc | 100 | 75 |
| 4-(2-aminoacetamido)-3-(3-methoxycarbonyl-2-thioureido)-4'-methyl-diphenyl thioether methanesulphonate | 10 | sc | 87 | 39 |
| 4-(3-methoxycarbonyl-2-thioureido)-3-(2-dimethyl-aminoacetamido)diphenyl ether hydrochloride | 10 | sc | 100 | 94 |
| 3-(3-methoxycarbonyl-2-thioureido)-4'-methyl-4-(2-dimethylaminoacetamido)-diphenyl thioether methanesulphonate | 10 | sc | 97 | 50 |
| 4-(3-methoxycarbonyl-2-thioureido)-3-(3-dimethyl-aminopropionamido)diphenyl thioether methanesulphonate | 10 | sc | 100 | 70 |
| 3-(2-diethylaminoacetamido)-4-(3-methoxycarbonyl-2-thio-ureido)diphenyl thioether methanesulphonate | 10 | sc | 100 | 98 |
| 4-allylthio-1-(3-methoxy-carbonyl-2-thioureido-2-(2-dimethylaminoacetamido)-benzene methanesulphonate | 10 | sc | 100 | 73 |
| 3-(2-dimethylaminoacetamido)-4-(3-methoxycarbonyl-2-thio-ureido)diphenyl ether hydrochloride | 10 | sc | 100 | 74 |
| 4-benzylthio-1-(3-methoxy-carbonyl-2-thioureido)-2-(2-dimethylaminoacetamido)-benzene methanesulphonate | 10 | sc | 100 | 60 |
| 4-(3-methoxycarbonyl-2-thioureido)-3-(2-dimethyl-aminopropionamido)diphenyl thioether methanesulphonate | 10 | sc | 100 | 100 |
| 4-cyclopentylthio-1-(3-methoxycarbonyl-2-thio-ureido)-2-(2-dimethylamino-acetamido)benzene methanesulphonate | 10 | sc | 100 | 100 |

TABLE V

| Test Compound | Form | Dose mg/kg animal body weight | Route of Administration | Age of infection when treated (days) | Percentage reducton in mean worm burdens | | | |
|---|---|---|---|---|---|---|---|---|
| | | | | | H. contortus | O. circumcincta | T. axei | T. colubriformis | N. spathiger |
| P | B | 4 | oral | 7 | 100 | 100 | 100 | 100 | 95 |
| | | | | 21 | 100 | 100 | 100 | 100 | 91 |
| | M | 25 | intramuscular | 7 | 100 | 100 | 100 | 100 | 84 |
| | | | | 21 | 100 | 100 | 100 | 100 | 100 |
| Q | M | 25 | sc | 7 | 100 | 58 | 100 | 97 | 49 |
| | | | | 21 | 100 | 100 | 100 | 100 | 97 |
| R | M | 25 | sc | 7 | 100 | 100 | 100 | 99 | 67 |
| | | | | 21 | 99 | 78 | 100 | 79 | 72 |
| | C | 4 | oral | 7 | 100 | 34 | 97 | 100 | 42 |
| | | | | 21 | 100 | 100 | 100 | 100 | 84 |
| S | C | 10 | oral | 7 | 100 | 96 | 100 | 100 | 94 |
| | | | | 21 | 100 | 100 | 100 | 100 | 100 |
| | C | 25 | sc | 7 | 100 | 66 | 100 | 98 | 57 |
| | | | | 21 | 98 | 97 | 100 | 96 | 21 |
| | B | 4 | oral | 7 | 100 | 99 | 100 | 100 | 67 |
| | | | | 21 | 100 | 100 | 100 | 94 | 73 |
| T | M | 25 | sc | 7 | 100 | 100 | 100 | 100 | 100 |
| | | | | 21 | 100 | 98 | 100 | 94 | 65 |
| U | M | 25 | sc | 7 | 100 | 100 | 100 | 100 | 95 |
| | | | | 21 | 100 | 100 | 100 | 100 | 97 |

D. Activity against mature and immature liver flukes in sheep

On the first day of the experiment, four sheep were infected with 300 metacercariae of *Fasciola hepatica* each, and on the 56th day the same four sheep were infected with a further 300 metacercariae of *F. hepatica* each.

On the 70th day, two the sheep (designated S1 and S2 in Table VI below) were each treated orally with 100 mg/kg animal body weight of 4-(3-methoxycarbonyl-2-thioureido)-3-(2-dimethylaminoacetamido)-diphenyl thioether contained in gelatin capsules, while the other two sheep (designated S3 and S4 in Table VI) were left untreated and used as control animals.

On the 98th day of the experiment, all four sheep were killed and inspected. For each sheep the numbers of mature flukes present in the bile ducts and the numbers of immature flukes present in the rest of the liver were counted, and the gall bladder was inspected for the presence of eggs. The results are expressed below in Table VI.

The livers of the control animals S3 and S4 were very fibrosed. The livers of the treated animals S1 and S2 showed signs of having been infected by flukes, but the scars were healing well and the livers were returning to normal when the sheep were killed.

TABLE VI

| Sheep | Treated Animals | | Control Animals | |
|---|---|---|---|---|
| | S1 | S2 | S3 | S4 |
| Number of mature flukes in bile ducts | 0 | 0 | 94 | 172 |
| Number of immature flukes in liver | 0 | 1 | 24 | 35 |
| Eggs in gall bladder | absent | absent | present | present |

Compounds of formula I wherein Z represents a group of formula II ($R^1$, $R^2$, $R^5$, $R^6$, $R^7$, A and $X^-$ being as hereinbefore defined) are particularly valuable as anthelmintics because of their solubility in water, especially such compounds wherein $X^-$ is a chloride or methanesulphonate ion.

Another class of particularly valuable anthelmintic compounds of formula I are those wherein $R^1$ represents a methyl group, $R^2$ represents a group of formula $-SR^3$, $-SOR^3$ or $-OR^3$ (wherein $R^3$ represents a straight- or branched-chain alkyl group containing from 2 to 4 carbon atoms, a cycloalkyl group containing from 3 to 7 carbon atoms, a benzyl group or a phenyl group), A represents a methylene [$-CH_2-$], ethylene [$-CH_2CH_2-$] or ethylidene [$-CH(CH_3)-$] group, and Z represents a group of formula II or III wherein $R^6$ and $R^7$ each represent a hydrogen atom or a straight- or branched-chain alkyl group containing from 1 to 3 carbon atoms and, in formula II (when present), $R^5$ represents a hydrogen atom and $X^-$ represents a halide (e.g. bromide, iodide or, preferably, chloride) ion or a methanesulphonate ion.

A class of compounds of formula I which are especially valuable as anthelmintics are those wherein $R^1$ represents a methyl group, $R^2$ represents a phenylthio or cyclopentylthio group, A represents a methylene, ethylene or ethylidene group, and Z represents a group of formula II or III wherein $R^6$ and $R^7$ each represent methyl groups and, in formula II (when present), $R^5$ represents a hydrogen atom and $X^-$ represents a chloride or methanesulphonate ion.

Of particular importance as an anthelmintic is 4-(3-methoxycarbonyl-2-thioureido)-3-(2-dimethylaminoacetamido)-diphenyl thioether and its pharmaceutically acceptable salts.

In addition to possessing anthelmintic activity, the new compounds of general formula I are also useful as agricultural pesticides, in particular as fungicides against species of fungi which are pathogenic to plants, and are also active as fungicides against fungal species which are pathogenic to animals.

For example, the compounds of formula I are of particular utility in fungicidal seed dressings, for example seed dressings for the protection of cereal seeds, and are also useful in combating grey moulds (e.g. *Botrytis spp.*) and brown moulds and storage rots of fruit and vegetables, for example grapes, peaches, lettuces and beans.

As fungicides for use against species of fungi pathogenic to plants, the compounds of formula I are particularly useful in the control of *Alternaria solani*, *Botrytis cinerea*, *Cercospora beticola*, *Cochliobolus sativus*, *Colletotrichum* spp., e.g. *C. gassypii*, *Fusarium* spp., e.g. *F. nivalae* and *F. roseum*, *Gloeosporium* spp., *Helminthosporium* spp., e.g. *H. avenae* and *H. gramineum*, *Mycosphaerella* spp., e.g. *M. pinodes* and *M. pomi*, *Nectria* spp., *Penicillium* spp., *Piricularia oryzae*, *Pythium* spp., *Rhizoctonia* spp., *Rhizopus nigricans*, *Sclerotinia* spp., e.g., *S. cinerea* and *S. sclerotiorum*, *Septoria nodurum*, *Tilletia caries*, *Ustilago avenae*, *Venturia inaequalis* and *Verticillium* spp., e.g., *V. alboatrum*.

The fungicidal properties of the compounds of formula I against plant pathogenic fungi have been demonstrated, for example, in the following test:

| Inhibition of Fungal Growth on Agar - in vitro | |
|---|---|
| Three fungal species were used: | Maintained on: |
| *Botrytis cinerea* (spores) | - potato dextrose agar |
| *Helminthosporium avenae* (mycelium) | - oatmeal agar and inoculated into Czapek Dox broth for preparation of mycelial suspension |
| *Mycospherella pinodes* (spores) | - Coon's agar |

All species were subcultured onto fresh maintenance media at weekly intervals.

Preparation of Fungal Suspensions

Spore suspensions were prepared by scraping agar slopes of 1 to 2 week old fungal cultures with sterile distilled water using a glass rod. The cultures were then filtered through muslin and the filtrate containing spores used for inoculation.

*H. avenae* inoculum was prepared by macerating a two week old liquid culture to give a fine suspension.

Preparation of Test Compound Suspensions

The test compound (0.025 g.) was ground with sterile distilled water [containing about 1.0 ml. of a 0.1% w/v solution of a wetting agent (Texofor FX 170) in sterile distilled water] with a "Teflon" block and the suspension obtained was made up to a volume of 50 ml. with sterile distilled water. Portions of this suspension containing 500 parts per million by weight (ppm) of test compound were then serially diluted with sterile distilled water to give suspensions containing 100 ppm and 20 ppm, respectively.

Test Procedure

Test tubes containing 4.0 ml. of molten potato dextrose agar at about 50° C. were inoculated with 0.5 ml. of the 500 ppm, 100 ppm or 20 ppm test compound suspension and 0.5 ml. of fungi suspension delivered with a sterile syringe to give a final concentration of test compound of 50 ppm, 10 ppm and 2 ppm respectively. Two replicate test tubes at each concentration of test compound were inoculated with each fungal species. Similar test tubes without antifungal agent were also inoculated in a similar fashion with the fungal suspensions. After inoculation of the molten agar, the test tubes were sloped and the agar allowed to set. The test tubes were then incubated at 25° C. for either 2 days [*B. cinerea* and *M. pinodes*] or 3 days [*H. avenae*]. The Minimum Effective Concentration (MEC) for each test compound against each fungal species was determined as the concentration at which two-thirds inhibition of fungal growth was obtained in comparison with the control test tubes containing potato dextrose agar and fungal suspension alone. The results are expressed below in Table VII.

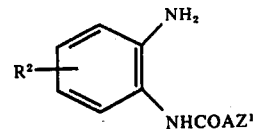

TABLE VII

| Test Compound | | MEC (ppm of test compound in agar) |
|---|---|---|
| 4-(3-Methoxycarbonyl-2-thioureido)-3-(2-dimethylaminoacetamido)diphenyl thioether | *b. cinerea* (spores) | >50 |
| | *H. avenae* >(mycelium) | <2 |
| | *M. pinodes* (spores) | >50 |
| 4-(2-Aminoacetamido)-3-(3-methoxycarbonyl-2-thioureido)diphenyl thioether | *B. cinerea* | 10–50 |
| | *H. avenae* | 2–10 |
| | *M. pinodes* | 10–50 |
| 4-(3-Methoxycarbonyl-2-thioureido)-3-(3-dimethylaminopropionamido)-diphenyl thioether | *B. cinerea* | 2–10 |
| | *H. avenae* | <2 |
| | *M. pinodes* | 10–50 |

The symbol ">" in the above Table means "greater than" and the symbol "<" means "less than".

Compounds of formula I wherein Z represents a group of formula II ($R^1$, $R^2$, $R^5$, $R^6$, $R^7$, A and $X^-$ being as hereinbefore defined) are particularly valuable as antifungal agents because of their solubility in water, especially such compounds wherein $X^-$ is a chloride or methanesulphonate ion.

Another class of particularly valuable compounds of formula I as antifungal agents are those wherein $R^1$ represents a methyl or ethyl group, $R^2$ represents a phenylthio group and Z represents a group of formula II wherein $R^5$, $R^6$ and $R^7$ each represents a hydrogen atom or a methyl group and $X^-$ represents a halide (e.g. chloride, bromide or iodide) ion or a methanesulphonate ion or of formula III wherein $R^6$ and $R^7$ each represents a hydrogen atom or a methyl group.

As a feature of the present invention, compounds of general formula I are prepared by the suitable adaptation of known methods, for example: (1) by the reaction of equimolecular quantities of an isothiocyanate of the general formula:

$$SCNCO_2R^1 \quad\quad IV$$

(wherein $R^1$ is as hereinbefore defined) and an amine of the general formula:

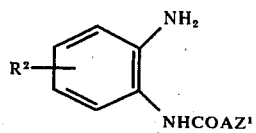   V (wherein $R^2$ and A are as hereinbefore defined and $Z^1$ represents a group of formula II, wherein $R^6$ and $R^7$ are as hereinbefore defined, $R^5$ represents a hydrogen atom and $X^-$ represents a halide ion, or of formula III as hereinbefore defined) to give a compound of formula I wherein $R^1$, $R^2$ and A are as hereinbefore defined, and Z represents the group $Z^1$ as hereinbefore defined (hereinafter referred to as "compounds of formula Ia").

The reaction may be carried out in the presence of an inert solvent, for example a lower alkanone, e.g. acetone or methyl ethyl ketone, a lower alkanol, e.g. methanol or ethanol, dioxan, ethyl acetate, acetonitrile or an aromatic hydrocarbon, e.g. toluene, at a temperature between 0° C. and 150° C. and preferably between 10° C. and 60° C., and optionally in the presence of acetic acid.

The isothiocyanates of formula IV may be prepared by the reaction of an ester of the general formula:

   VI (wherein $R^1$ is as hereinbefore defined and $X^1$ is a bromine, iodine or, preferably, chlorine atom) and a thiocyanate of the general formula:

   VII wherein M is a metal, preferably an alkali metal or an alkaline earth metal, atom and q is the valency of that metal. The reaction may be carried out in the presence of an inert organic solvent, for example a lower alkanone, e.g. acetone, ethyl acetate or acetonitrile, at a temperature between 0° C. and 100° C., and preferably between 20° C. and 60° C.

The preparation of compounds of formula IV may be effected in situ for subsequent reaction with compounds of formula V or, if desired, the compounds of formula IV may be isolated by known methods prior to reaction with compounds of formula V. 2. by the reaction of an amine of the general formula:

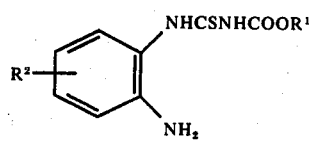   VIII (wherein $R^1$ and $R^2$ are as hereinbefore defined) with a compound of the general formula:

   IX (wherein $X^1$ and A are as hereinbefore defined, and $Z^2$ represents a group $Z^1$ as hereinbefore defined with the exception that neither $R^6$ nor $R^7$ can represent a hydrogen atom) to give a compound of formula I wherein $R^1$, $R^2$ and A are as hereinbefore defined and Z represents the group $Z^2$ as hereinbefore defined, hereinafter referred to as "compounds of formula Ib". The reaction is preferably carried out in an organic solvent, e.g. toluene or dimethylformamide, at a temperature between 0° C. and the reflux temperature of the reaction mixture.

The compounds of formula IX may be prepared by the reaction of a compound of the general formula:

   X (wherein A and $Z^2$ are as hereinbefore defined) with a reactive acid halide, e.g. phosphorus pentachloride. If desired, the compounds of formula IX may be prepared in situ.

3. by the reaction of an amine of general formula VIII with a compound of formula X (wherein A and $Z^2$ are as hereinbefore defined) in the presence of a condensing agent, e.g. phosphorus oxychloride, in a suitable solvent, e.g. dimethylformamide or dichloromethane, at a temperature between 0° C. and the reflux temperature of the reaction mixture, to give a compound of formula Ib.

4. by reaction of a compound of the general formula:

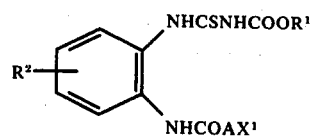   XI (wherein $R^1$, $R^2$, A and $X^1$ are as hereinbefore defined) with a. a compound of the general formula:

   XII (wherein $R^6$ and $R^7$ are as hereinbefore defined), an excess of which may be employed as an acid-binding agent, to give a compound of formula Ia, or b. a compound of the general formula:

   XIII (wherein $R^6$ and $R^7$ are as hereinbefore defined, and $R^5$ represents a straight- or branched-chain alkyl group containing not more than 4 carbon atoms) to give a compound of formula I wherein $R^1$, $R^2$ and A are as hereinbefore defined and Z is a group of formula II wherein $R^5$ is a straight- or branched-chain alkyl group containing not more than 4 carbon atoms, $R^6$ and $R^7$ are as hereinbefore defined and the anion $X^-$ is a halide ion derived from the halogen atom represented by $X^1$ in the compound of formula XI.

The reaction between the compound of formula XI and the compound of formula XII may be carried out in an inert organic solvent, for example a lower alkanol, e.g. ethanol, or an aromatic hydrocarbon, e.g. benzene or toluene, at a temperature between 20° C. and 100° C., preferably at room temperature or at the reflux temperature of the reaction mixture.

The reaction between the compound of formula XI and the compound of formula XIII may be carried out in an inert organic solvent, for example ethyl acetate or diethyl ether, at a temperature between 20° C. and 80° C., and preferably at the reflux temperature of the reaction mixture. 5. by reaction of a compound of formula I, wherein $R^1$, $R^2$ and A are as hereinbefore defined and Z represents a group of formula III (wherein $R^6$ and $R^7$ are as hereinbefore defined) with a compound of the general formula:

$$R^5X^2 \qquad \text{XIV}$$

(wherein $R^5$ is as hereinbefore defined and $X^2$ is an atom or group corresponding to the anion $X^-$) to give a compound of formula I wherein $R^1$, $R^2$ and A are as hereinbefore defined and Z is a group of formula II, wherein $R^5$, $R^6$ and $R^7$ are as hereinbefore defined and the anion $X^-$ is derived from the atom or group represented by the symbol $X^2$ in the compound of formula XIV. The reaction is preferably carried out in an inert organic solvent, for example ethanol, ethyl acetate, acetone or diethyl ether, at a temperature between 10° C. and 40° C. 6. by reaction of a compound of the general formula:

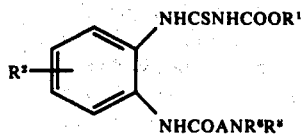

XV wherein A, $R^1$, $R^2$ and $R^6$ are as hereinbefore defined, and $R^8$ is a suitable protecting group, e.g. benzyloxycarbonyl, with a reagent for removing the said protecting group, e.g. a solution of hydrogen bromide in glacial acetic acid, to give a compound of formula I wherein $R^7$ (in the definition of Z) represents a hydrogen atom, the various other symbols being as hereinbefore defined. 7. by treatment of a compound of formula I wherein Z represents a group of formula II wherein $R^5$ represents a hydrogen atom ($R^1$, $R^2$, $R^6$, $R^7$, A and $X^-$ being as hereinbefore defined) with a base, to give a compound of formula I wherein $R^1$, $R^2$ and A are as hereinbefore defined and Z represents a group of formula III.

The reaction is preferably carried out by means of a carbonate or hydroxide of an alkali metal in the presence of water, generally at room temperature, and may optionally be carried out in situ without isolation of the compound of formula I wherein Z represents a group of formula II from the reaction mixture in which it is produced by means of some one of the reactions hereinbefore described.

Compounds of formula V may be prepared by the reduction of compounds of the general formula:

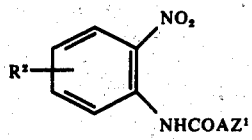

XVI (wherein $R^2$, A and $Z^1$ are as hereinbefore defined) by known methods for the reduction of aromatic nitro groups to amino groups, for example by hydrogenation in the presence of a hydrogenation catalyst, e.g. platinum or palladium, or by the use of ferrous chloride and reduced iron powder.

Compounds of formula XVI may be prepared by the reaction of a compound of the general formula:

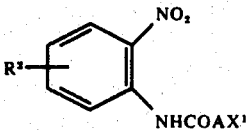

XVII (wherein $R^2$, A and $X^1$ are as hereinbefore defined with a compound of formula XII, an excess of which may be employed as an acid-binding agent, under the conditions hereinbefore described for the reaction of compounds of formula XI with compounds of formula XII.

Compounds of formula XVII may be prepared by the reaction of a compound of the general formula:

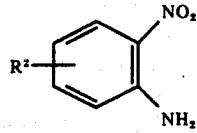

XVIII (wherein $R^2$ is as hereinbefore defined) with a compound of the general formula:

$$X^1COAX^1 \qquad \text{XIX}$$

wherein A and $X^1$ are as hereinbefore defined. The reaction is preferably carried out in an inert organic solvent, for example a lower alkanone, e.g. acetone, or an aromatic hydrocarbon, e.g. toluene, at a temperature between 0° C. and 110° C.

Compounds of formula V, wherein $R^2$, A and $Z^1$ are as hereinbefore defined, may be prepared from compounds of the general formula:

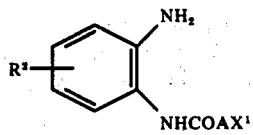

XX (wherein $R^2$, A and $X^1$ are as hereinbefore defined) by the application of processes hereinbefore described for the preparation of compounds of formula I from compounds of formula XI.

Compounds of formula XX may be prepared by the reduction of compounds of formula XVII by known methods for the reduction of aromatic nitro groups, for example as hereinbefore described for the reduction of compounds of general formula XVI.

Compounds of formula XI may be prepared by the reaction of a compound of formula XX with an isothiocyanate of formula IV. The reaction may be carried out under the conditions hereinbefore described for the reaction of compounds of formula IV with compounds of formula V to give compounds of formula I.

Compounds of formula XI may alternatively be prepared by the reaction of a compound of formula VIII with a compound of formula XIX. The reaction may be carried out under the conditions hereinbefore described for the reaction of compounds of formula XVIII with compounds of formula XIX to give compounds of formula XVII.

Compounds of formula XV may be prepared
  a. by reaction of an amine of formula VIII with a compound of the general formula:

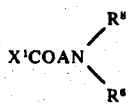

XXI wherein A, $R^6$, $R^8$ and $X^1$ are as hereinbefore defined. The reaction is preferably carried out in an organic solvent, e.g. dimethylformamide, at a temperature between 0° C. and the reflux temperature of the reaction mixture.

Compounds of formula XXI may be prepared by the reaction of a compound of the general formula:

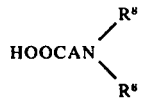   XXII (wherein A, $R^6$ and $R^8$ are as hereinbefore defined) with a reactive acid halide, e.g. phosphorus pentachloride.

b. by the reaction of an amine of formula VIII with a compound of formula XXII in the presence of phosphorus oxychloride in a suitable solvent, e.g. dimethylformamide, at a temperature between 0° C. and the reflux temperature of the reaction mixture.

c. by the reaction of a compound of the general formula:

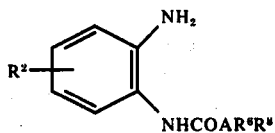   XXIII (wherein A, $R^2$, $R^6$ and $R^8$ are as hereinbefore defined) with a compound of formula IV by methods hereinbefore described for the preparation of compounds of formula I from amines of formula V.

Compounds of formula XXIII may be prepared by the reduction of compounds of formula:

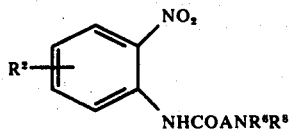   XXIV (wherein A, $R^2$, $R^6$ and $R^8$ are as hereinbefore defined) by known methods for the reduction of aromatic nitro groups to amino groups, for example by the use of ferrous chloride and reduced iron powder.

Compounds of formula XXIV may be prepared by the reaction of compounds of formula XVIII with compounds of formula XXI or XXII by methods hereinbefore described for the preparation of compounds of formula XV.

By the term 'known methods' as used in the present specification is meant methods heretofore used or described in the chemical literature.

The following Examples illustrate the preparation of the new compounds according to the present invention.

EXAMPLE 1

A solution of 4-amino-3-(2-dimethylaminoacetamido)diphenyl thioether (6.4 g.) in dry acetone (100 ml.) was stirred during the dropwise addition of methoxycarbonyl isothiocyanate (2.7 g.), the temperature being maintained between 15° C. and 20° C. by external cooling and afterwards at the same temperature for a further 20 minutes. The solution was concentrated in vacuo to form a yellow oil which was triturated with diethyl ether. The solid product was recrystallised from isopropanol to give 4-(3-methoxycarbonyl-2-thioureido)-3-(2-dimethylaminoacetamido)diphenyl thioether (4.0 g.), in the form of a pale buff solid, m.p. 143°–144° C. (with decomposition).

The 4-amino-3-(2-dimethylaminoacetamido)diphenyl thioether, used as starting material, was prepared as follows:

Thiophenol (44 g.) was added, over a period of 5 minutes and under an atmosphere of dry nitrogen, to a suspension of 5-chloro-2-nitro-aniline (66.5 g.; prepared according to Fuson et al, J. Org. Chem., 12, 799–806, 1947) and anhydrous potassium carbonate (60.6 g.) in dimethylformamide (200 ml.). The reaction mixture was heated under reflux for 8 hours and then cooled. Water (200 ml.) was added dropwise whilst maintaining the temperature at 5°–10° C. The precipitated solid was filtered off, washed well with water and recrystallised from isopropanol, to give 3-amino-4-nitro-diphenyl thioether (83 g.), m.p. 117°–118° C., in the form of a pale brown solid.

Chloroacetyl chloride (6.2 g.) was added to a stirred solution of 3-amino-4-nitro-diphenyl thioether (12.3 g.) in dry toluene (50 ml.). The solution was heated at reflux for 1 hour. The hot solution was added to petrol (80 ml.; b.p. 60°–80° C.), whereupon 3-(2-chloroacetamido)-4-nitrodiphenyl thioether crystallised in the form of a yellow solid (15.8 g.), m.p. 152°–154° C.

A solution of dimethylamine in ethanol (33% w/v; 60 ml.) was added to a suspension of 3-(2-chloroacetamido)-4-nitrodiphenyl thioether (15.5 g.) in ethanol (140 ml.). The suspension was stirred and heated at reflux for one hour. The cooled solution was concentrated in vacuo to give a yellow solid. The solid was washed with ice-cold ethanol (10 ml.) and then suspended in water (100 ml.). The solid was filtered off, washed with water and dried at 80° C., to give 3-(2-dimethylaminoacetamido)-4-nitrodiphenyl thioether (14.9 g.).

To a solution of 3-(2-dimethylaminoacetamido)-4-nitrodiphenyl thioether (14.9 g.) in ethyl acetate (200 ml.), there was added palladium on charcoal catalyst (6 g.; 5% Pd w/w). The suspension was shaken in an atmosphere of hydrogen at atmospheric pressure and room temperature.

After 90 minutes 3.1 liters of hydrogen had been absorbed. The solution was filtered and concentrated in vacuo to give 4-amino-3-(2-dimethylaminoacetamido)-diphenyl thioether (12.9 g.) in the form of a white solid, m.p. 131°–133° C.

EXAMPLE 2

To a stirred solution of 4-amino-3-(3-methoxycarbonyl-2-thioureido)diphenyl thioether (7.9 g.) in dimethylformamide (50 ml.) there was added during 5 minutes N,N-dimethylglycyl chloride hydrochloride (3.8 g.). The reaction temperature rose to 37° C. during the addition and a white solid began to separate. The reaction mixture was then stirred and heated at 40°–45° C. for 75 minutes, cooled and diluted with acetone (150 ml.). The solid was collected on a filter, washed with acetone and sucked dry. This solid was dissolved in a boiling mixture of methanol (100 ml.) and water (10 ml.), and the solution was treated with decolourising charcoal, filtered hot and allowed to crystallise to give 3-(3-methoxycarbonyl-2-thioureido)-4-(2-dimethylaminoacetamido)diphenyl thioether hydrochloride (5.25 g.), in the form of a white crystalline solid, m.p. 192°–193° C. (with decomposition).

The 4-amino-3-(3-methoxycarbonyl-2-thioureido)-diphenyl thioether, used as starting material, was prepared as follows:-

Methoxycarbonyl isothiocyanate (12 g.) was added dropwise during 5 minutes to a stirred solution of 3-amino-4-nitrodiphenyl thioether (prepared as hereinbefore described in Example 1; 12.3 g.) in acetonitrile (90 ml.). The reaction temperature was maintained at 15°–20° C. during the addition by external cooling. The mixture was then warmed to 40°–45° C. and stirred for a further 5 hours, during which time a yellow solid separated. The reaction mixture was cooled in ice and filtered. The residue was washed with diethyl ether and dried to give 3-(3-methoxycarbonyl-2-thioureido)-4-nitrodiphenyl thioether (12.9 g.), m.p. 144°–145° C. (with decomposition).

Reduced iron powder (11.1 g.) was added portionwise, during 5 minutes, to a rapidly stirred mixture of 3-(3-methoxycarbonyl-2-thioureido)-4-nitrodiphenyl thioether (12.1 g.) and ferrous chloride tetrahydrate (2.2 g.) in methanol (167 ml.) and water (37 ml.) heated at reflux. After 90 minutes the black suspension was diluted with methanol (150 ml.), filtered hot through a Hyflo bed and the Hyflo bed was washed twice with hot methanol (2 × 50 ml.). The combined solution was re-heated, treated with decolourising charcoal, filtered hot and then concentrated under reduced pressure to about one half its volume. The off-white solid which separated was filtered after cooling, sucked dry on the filter and recrystallized from a mixture of methanol (450 ml.) and water (250 ml.) to give 4-amino-3-(3-methoxycarbonyl-2-thioureido)-diphenyl thioether (8.1 g.), m.p. 164°–165° C.

EXAMPLE 3

A solution of 4-(3-methoxycarbonyl-2-thioureido)-3-(2-dimethylaminoacetamido)diphenyl thioether (1.0 g.; prepared as hereinbefore described in Example 1) in the minimum volume of acetone was treated with an excess of a saturated solution of hydrogen chloride in anhydrous diethyl ether. The solid which rapidly crystallised was filtered off and recrystallised from ethanol to give 4-(3-methoxycarbonyl-2-thioureido)-3-(2-dimethylaminoacetamido)diphenyl thioether hydrochloride (0.7 g.), m.p. 194°–195° C. (with decomposition).

EXAMPLE 4

A solution of 4-(3-methoxycarbonyl-2-thioureido)-3-(2-dimethylaminoacetamido)diphenyl thioether (5.0 g.; prepared as hereinbefore described in Example 1) in acetone (80 ml.) was treated with a solution of methanesulphonic acid (1.2 g.) in acetone (20 ml.). After allowing the mixture to stand for 30 minutes, the precipitated solid was filtered off and recrystallised from ethanol to give 4-(3-methoxycarbonyl-2-thioureido)-3-(2-dimethylaminoacetamido)diphenyl thioether methanesulphonate (4.2 g.), m.p. 169°–171° C. (with decomposition).

EXAMPLE 5

A solution of 4-(3-methoxycarbonyl-2-thioureido)-3-(2-dimethylaminoacetamido)diphenyl thioether (1.25 g.; prepared as hereinbefore described in Example 1) in acetone (30 ml.) was treated, with shaking, with maleic acid (0.35 g.). The solid rapidly dissolved and the mixture was left to stand overnight. The resulting solid was filtered off, washed with cold acetone (10 ml.) and recrystallised from ethanol to give 4-(3-methoxycarbonyl-2-thioureido)-3-(2-dimethylaminoacetamido)-diphenyl thioether maleate (0.8 g.), m.p. 121°–123° C. (with decomposition).

EXAMPLE 6

By proceeding in a manner similar to that hereinbefore described in Example 2 but replacing the 4-amino-3-(3-methoxycarbonyl-2-thioureido)diphenyl thioether, used as starting material, by the appropriate quantities of 4-amino-4'-chloro-3-(3-methoxycarbonyl-2-thioureido)diphenyl thioether, 4-amino-3-(3-methoxycarbonyl-2l -thioureido)-4'-methyldiphenyl thioether, 3-amino-4-(3-methoxycarbonyl-2-thioureido)diphenyl ether, 2-amino-1-(3-methoxycarbonyl-2-thioureido)-4-methylthiobenzene, and 4-allylthio-2-amino-1-(3-methoxycarbonyl-2-thioureido)benzene, respectively, there were prepared 4'-chloro-3-(3-methoxycarbonyl-2-thioureido)-4-(2-dimethylaminoacetamido)diphenyl thioether hydrochloride, m.p. 183°–185° C. (with decomposition), 3-(3-methoxycarbonyl-2-thioureido)-4'-methyl-4-(2-dimethylaminoacetamido)diphenyl thioether hydrochloride, m.p. 181°–184° C. (with decomposition), 4-(3-methoxycarbonyl-2-thioureido)-3-(2-dimethylaminoacetamido)diphenyl ether hydrochloride, m.p. 164°–165° C. (with decomposition), 2-(3-methoxycarbonyl-2-thioureido)-4-methylthio-2-dimethylaminoacetamido)benzene hydrochloride, m.p. 166°–167° C., and 4-allylthio-1-(3-methoxycarbonyl-2-thioureido)-2-(2-dimethylaminoacetamido)benzene hydrochloride, m.p. 177°–178° C. (with decomposition).

The starting materials were prepared as follows:- a. By proceeding in a manner similar to that hereinbefore described in Example 2 but replacing the 3-(3-methoxycarbonyl-2-thioureido)-4-nitrodiphenyl thioether, used as starting material, by the appropriate quantities of 4'-chloro-3-(3-methoxycarbonyl-2-thioureido)-4-nitrodiphenyl thioether, 3-(3-methoxycarbonyl-2-thioureido)-4'-methyl-4-nitrodiphenyl thioether, 4-(3-methoxycarbonyl-2-thioureido)-3-nitrodiphenyl ether, 1-(3-methoxycarbonyl-2-thioureido)-4-methylthio-2-nitrobenzene, and 4-allylthio-1-(3-methoxycarbonyl-2-thioureido)-2-nitrobenzene, respectively, there were prepared 4-amino-4'-chloro-3-(3-methoxycarbonyl-2-thioureido)diphenyl thioether, m.p. 162°–163° C., 4-amino-3-(3-methoxycarbonyl-2-thioureido)-4'-methyldiphenyl thioether, m.p. 143°–145° C., 3-amino-4-(3-methoxycarbonyl-2-thioureido)diphenyl ether, m.p. 184°–186° C. (with decomposition), 2-amino-1-(3-methoxycarbonyl-2-thioureido)-4-methyl-thiobenzene, m.p. 167°–169° C., and 4-allylthio-2-amino-1-(3-methoxycarbonyl-2-thioureido)-benzene, m.p. 164°–165° C. (with decomposition).

b. Methyl chloroformate (39.3 ml.) was added in one portion to a stirred suspension of dry potassium thiocyanate (43.4 g.) in acetonitrile (540 ml.) and the mixture was stirred for one hour at room temperature.

3-Amino-4'-chloro-4-nitro-diphenyl thioether (42.4 g.) was added and the mixture was stirred at room temperature for 2 hours and then at 40°–50° C. for 3 hours. The mixture was then poured into water (2 liters) and the solid which formed was filtered off and recrystallised from a mixture of ethanol and dimethylformamide to give 4'-chloro-3-(3-methoxycarbonyl-2-thioureido)-4-nitrodiphenyl thioether (42.3 g.), m.p. 169° C. (with decomposition).

By proceeding in a similar manner but replacing the 3-amino-4'-chloro-4-nitrodiphenyl thioether by the appropriate quantities of 3-amino-4'-methyl-4-nitrodiphenyl thioether,
4-amino-3-nitro-diphenyl ether,
4-methylthio-2-nitroaniline, and
4-allylthio-2-nitroaniline,
respectively, there were prepared
3-(3-methoxycarbonyl-2-thioureido)-4'-methyl-4-nitrodiphenyl thioether, m.p. 148°–150° C. (with decomposition),
4-(3-methoxycarbonyl-2-thioureido)-3-nitrodiphenyl ether, m.p. 138°–140° C., 1-(3-methoxycarbonyl-2-thioureido)-4-methylthio-2-nitrobenzene, m.p. 152°–154° C., and
4-allylthio-1-(3-methoxycarbonyl-2-thioureido)-2-nitrobenzene, m.p. 121°–123° C.

c. (i) By proceeding in a manner similar to that hereinbefore described in Example 1 but replacing the thiophenol used as starting material by the appropriate quantities of 4-chlorothiophenol and 4-methyl(thiophenol) respectively, there were prepared
3-amino-4'-chloro-4-nitro-diphenyl thioether, m.p. 118°–120° C., and
3-amino-4'-methyl-4-nitro-diphenyl thioether, m.p. 103°–104° C.

ii. A stirred mixture of 4-acetamido-3-nitrodiphenyl ether [38 g.; prepared as described in J. A. C. S., 68, 1548 (1946)], water (57 ml.) and concentrated sulphuric acid (75 ml.) was heated at reflux for five minutes. The mixture was then cooled, poured into icewater (500 ml.) and made alkaline by the addition of concentrated aqueous ammonia solution. The mixture was extracted with chloroform (3 × 400 ml.), the extract was dried over magnesium sulphate and evaporated to give
4-amino-3-nitro-diphenyl ether (28 g.), in the form of a red oil which was used in the next stage without further purification.

iii. 2-Nitro-4-thiocyanato-aniline (17.6 g.) was added portionwise to a stirred solution of potassium hydroxide (13.4 g.) in ethanol (210 ml.) cooled below 15° C. After 5 minutes, methyl iodide (12.8 g.) was added to the purple solution and the mixture was allowed to stand overnight at room temperature. The mixture was then poured into water (1100 ml.) and the deep red solid was filtered off, washed with water, and dried to give 4-methylthio-2-nitroaniline (15.8 g.), m.p. 72°–73° C.

By proceeding in a similar manner but replacing the methyl iodide used as a starting material by the appropriate quantity of allyl bromide, there was prepared 4-allylthio-2-nitroaniline, in the form of a red oil.

A stirred mixture of o-nitroaniline (82.5 g.), dry sodium thiocyanate (180 g.) and acetic acid (1 liter) was treated at 11°–12° C. with a solution of bromine (96.5 g.) in acetic acid (100 ml.). The stirring was continued for a further hour at 11°–12° C. and the mixture was then allowed to warm to 15° C. and poured into water (3.5 liters). The yellow solid was filtered off, washed with water, and dissolved in acetone (1 liter). The solution was filtered and the filtrate was evaporated to give 2-nitro-4-thiocyanato-aniline (107 g.), m.p. 110°–112° C.

EXAMPLE 7

3-(3-Methoxycarbonyl-2-thioureido)-4'-methyl-4-(2-dimethylaminoacetamido)diphenyl thioether hydrochloride (6.92 g.; prepared as hereinbefore described in Example 6) was suspended in a mixture of water (100 ml.) and chloroform (170 ml.), and the suspension was treated with a solution of sodium carbonate (1.57 g.) in water (50 ml.), and stirred vigorously for 15 minutes. The organic layer was separated and the aqueous layer was extracted with chloroform (100 ml.). The organic layers were combined, washed with water, dried over magnesium sulphate and evaporated. The resulting oil solidified on scratching and was recrystallised from ethanol to give 3-(3-methoxycarbonyl-2-thioureido)-4'-methyl-4-(2-dimethylaminoacetamido)diphenyl thioether (3.7 g.), m.p. 146°–147° C. (with decomposition).

By proceeding in a similar manner but replacing the 3-(3-methoxycarbonyl-2-thioureido)-4'-methyl-4-(2-dimethylaminoacetamido)diphenyl thioether hydrochloride used as a starting material by the appropriate quantities of
2-(3-methoxycarbonyl-2-thioureido)-4-(2-dimethylaminoacetamido)diphenyl thioether hydrochloride (prepared as hereinbefore described in Example 2),
4'-chloro-3-(3-methoxycarbonyl-2-thioureido)-4-(2-dimethylaminoacetamido)diphenyl thioether hydrochloride (prepared as hereinbefore described in Example 6),
4-(3-methoxycarbonyl-2-thioureido)-3-(2-dimethylaminoacetamido)diphenyl ether hydrochloride (prepared as hereinbefore described in Example 6),
1-(3-methoxycarbonyl-2-thioureido)-2-(2-dimethylaminoacetamido)-4-methylthiobenzene hydrochloride (prepared as hereinbefore described in Example 6), and 4-allylthio-1-(3-methoxycarbonyl-2-thioureido)-2-(2-dimethylaminoacetamido)benzene hydrochloride (prepared as hereinbefore described in Example 6), respectively, there were prepared
3-(3-methoxycarbonyl-2-thioureido)-4-(2-dimethylaminoacetamido)diphenyl thioether, m.p. 149°–150° C. (with decomposition),
4'-chloro-3-(3-methoxycarbonyl-2-thioureido)-4-(2-dimethylaminoacetamido(diphenyl thioether, m.p. 170°–172° C.,
4-(3-methoxycarbonyl-2-thioureido)-3-(2-dimethylaminoacetamido)diphenyl ether, m.p. 159°–161° C. (with decomposition),
1-(3-methoxycarbonyl-2-thioureido)-2-(2-dimethylaminoacetamido)-4-methylthiobenzene, m.p. 142°–143° C. (with decomposition), and
4-allylthio-1-(3-methoxycarbonyl-2-thioureido)-2-(2-dimethylaminoacetamido)benzene, m.p. 133°–134° C. (with decomposition).

EXAMPLE 8

A stirred solution of 2-amino-4-ethylthio-1-(3-methoxycarbonyl-2-thioureido)benzene (8.35 g.) in dry dimethylformamide (60 ml.) was treated at room temperature with N,N-dimethylglycyl chloride hydrochloride (5.53 g.). The mixture was heated to 40°–50° C. for 45 minutes, then cooled, and diluted with diethyl ether (900 ml.). An oil precipitated which crystallised on standing. This solid was filtered off, washed with diethyl ether (100 ml.), and suspended in a mixture of chloroform (100 ml.) and water (100 ml.). Sodium carbonate (3.5 g.) was added and the mixture was stirred for 20 minutes. The chloroform layer was separated and the aqueous layer was extracted twice with chloroform (2 × 50 ml.). The organic layers were combined, dried over magnesium sulphate and evaporated to dryness. The residual solid was recrystallised from isopropanol to give 4-ethylthio-1-(3-methoxycarbonyl-2-thioureido)-2-(2-dimethylaminoacetamido)benzene (8.5 g.), m.p. 142° C. (with decomposition).

By proceeding in a similar manner but replacing the 2-amino-4-ethylthio-1-(3-methoxycarbonyl-2-thioureido)-benzene used as starting material by the appropriate quantities of 2-amino-4-benzylthio-1-(3-methoxycarbonyl-2-thioureido)-benzene, 2-amino-4-n-butylthio-1-(3-methoxycarbonyl-2-thioureido)benzene, 2-amino-4-cyclopentylthio-1-(3-methoxycarbonyl-2-thioureido)benzene, and 2-amino-4-(2-ethylthioethylthio)-1-(3-methoxycarbonyl-2-thioureido)benzene, respectively, there were prepared 4-benzylthio-1-(3-methoxycarbonyl-2-thioureido)-2-(2-dimethylaminoacetamido)benzene, m.p. 115°–116° C., 4-n-butylthio-1-(3-methoxycarbonyl-2-thioureido)-2-(2-dimethylaminoacetamido)benzene, m.p. 104°–106° C., 4-cyclopentylthio-1-(3-methoxycarbonyl-2-thioureido)-2-(2-dimethylaminoacetamido)benzene, m.p. 126°–130° C. (with decomposition), and 4-(2-ethylthioethylthio)-1-(3-methoxycarbonyl-2-thioureido)-2-(2-dimethylaminoacetamido)benzene, m.p. 86°–87° C.

The starting materials were prepared as follows:- a. A mixture of 4-ethylthio-1-(3-methoxycarbonyl-2-thioureido)-2-nitrobenzene (14.0 g.), ferrous chloride tetrahydrate (3.04 g.), methanol (235 ml.) and water (50 ml.) was heated to reflux and treated with reduced iron powder (15.5 g.) portionwise during 5 minutes. The mixture was heated at reflux with stirring for 1 hour. Methanol (250 ml.) was added and the mixture was again heated to reflux. The hot mixture was filtered and the filtrate was allowed to cool to room temperature. The solid which crystallised on cooling was filtered off to give 2-amino-4-ethylthio-1-(3-methoxycarbonyl-2-thioureido)benzene (7.5 g.), m.p. 168° C.

By proceeding in a similar manner but replacing the 4-ethylthio-1-(3-methoxycarbonyl-2-thioureido)-2-nitrobenzene used as a starting material by the appropriate quantities of 4-benzylthio-1-(3-methoxycarbonyl-2-thioreido)-2-nitrobenzene, 4-n-butylthio-1-(3-methoxycarbonyl-2-thioureido)-2-nitrobenzene, 4-cyclopentylthio-1-(3-methoxycarbonyl-2-thioureido)-2-nitrobenzene, and 4-(2-ethylthioethylthio)-1-(3-methoxycarbonyl-2-thioureido)-2-nitrobenzene, respectively, there were prepared 2-amino-4-benzylthio-1-(3-methoxycarbonyl-2-thioureido)-benzene, m.p. 191°–193° C., 2-amino-4-n-butylthio-1-(3-methoxycarbonyl-2-thioureido)-benzene, m.p. 164°–165° C., 2-amino-4-cyclopentylthio-1-(3-methoxycarbonyl-2-thioureido)benzene, m.p. 169°–172° C., and 2-amino-4-(2-ethylthioethylthio)-1-(3-methoxycarbonyl-2-thioureido)benzene, m.p. 151°–153° C.

b. A mixture of dry potassium thiocyanate (25.65 g.) and acetonitrile (320 ml.) was cooled to 10° C. and treated during 5 minutes with methyl chloroformate (25.0 g.). The mixture was stirred at room temperature for 2 hours. 1-Amino-4-ethylthio-2-nitrobenzene (22.45 g.) was then added to the mixture at 10°–15° C. The suspension was stirred for 3 hours at room temperature and allowed to stand overnight. It was then poured into water (1.6 liters) and the solid which precipitated was filtered off, washed with water and recrystallised from a mixture of methanol and ethanol, to give 4-ethylthio-1-(3-methoxycarbonyl-2-thioureido)-2-nitrobenzene (14.0 g.), m.p. 152° C.

By proceeding in a similar manner but replacing the 1-amino-4-ethylthio-2-nitrobenzene used as starting material by the appropriate quantities of 1-amino-4-benzylthio-2-nitrobenzene, 1-amino-4-n-butylthio-2-nitrobenzene, 1-amino-4-cyclopentylthio-2-nitrobenzene, and 1-amino-4-(2-ethylthioethylthio)-2-nitrobenzene, respectively, there were prepared 4-benzylthio-1-(3-methoxycarbonyl-2-thioureido)-2-nitrobenzene, m.p. 172°–174° C. (with decomposition), 4-n-butylthio-1-(3-methoxycarbonyl-2-thioureido)-2-nitrobenzene, m.p. 129°–131° C., 4-cyclopentylthio-1-(3-methoxycarbonyl-2-thioureido)-2-nitrobenzene, m.p. 123° C., and 4-(2-ethylthioethylthio)-1-(3-methoxycarbonyl-2-thioureido)-2-nitrobenzene, m.p. 130°–131° C. (c) 2-Nitro-4-thiocyanatoaniline (17.55 g.; prepared as hereinbefore described in Example 6) was added portionwise to a stirred solution of potassium hydroxide (13.4 g.) in ethanol (210 ml.), keeping the temperature below 20° C. After 5 minutes, ethyl iodide (14.4 g.) was added during 5 minutes. The stirring was continued for a further hour and the mixture was allowed to stand overnight. The mixture was then poured into water (1100 ml.) and extracted with chloroform (3 × 300 ml.). The chloroform layers were combined, washed with water (500 ml.), dried over magnesium sulphate, and evaporated to give 1-amino-4-ethylthio-2-nitrobenzene (17.0 g.), in the form of a red oil.

By proceeding in a similar manner but replacing the ethyl iodide used as a starting material by the appropriate quantities of benzyl bromide, n-butyl iodide, cyclopentyl bromide, and 2-ethylthioethyl chloride, respectively, there were prepared 1-amino-4-benzylthio-2-nitrobenzene, m.p. 97°–99° C., 1-amino-4-n-butylthio-2-nitrobenzene, in the form of a red oil, 1-amino-4-cyclopentylthio-2-nitrobenzene, in the form of a brown oil, and 1-amino-4-(2-ethylthioethylthio)-21-nitrobenzene in the form of a red oil.

EXAMPLE 9

A stirred solution of 3-amino-4-(3-methoxycarbonyl-2-thioureido)diphenyl sulphoxide (0.5 .) in dry dimethylformamide (5 ml.) was treated at room temperature with N,N-dimethylglycyl chloride hydrochloride (0.32 g.). After 90 minutes the solution was poured into diethyl ether (50 ml.). The resulting oil solidified, and the solid was filtered off and recrystallised from a mixture of methanol and diethyl ether to give 4-(3-methoxycarbonyl-2-thioureido)-3-(2-dimethylaminoacetamido)diphenyl sulphoxide hydrochloride (0.1 g.), m.p. 195°–197° C.

The 3-amino-4-(3-methoxycarbonyl-2-thioureido)-diphenyl sulphoxide, used as starting material, was prepared as follows:-

4-Acetamidodiphenyl sulphide [24.8 g.; prepared as described in Farmaco (Ed. Sci.), 14, 288-303, (1969)] was dissolved in ethanol (200 ml.) and the solution treated at 40°–45° C. with hydrogen peroxide solution (100 volume; 23 ml.). The mixture was then heated at reflux for 6 hours, a further quantity of hydrogen peroxide (7 ml.) was added, and the heating at reflux was continued for a further 6 hours. The excess hydrogen peroxide was destroyed by the addition of manganese dioxide (1 g.) and heating at reflux for 20 minutes. The solution was filtered and the filtrate was added to water (1,250 ml.). The resulting solid was filtered off to give 4-acetamidodiphenyl sulphoxide (20.8 g.), m.p. 140°–142° C.

4-Acetamidodiphenyl sulphoxide (16.7 g.) was dissolved in a mixture of glacial acetic acid (10 ml.), acetic anhydride (13 ml.), and concentrated sulphuric acid (0.42 ml.). The mixture was cooled to 0° C. and a solution of nitric acid (96% w/w; 4.4 ml.) in glacial acetic acid (7 ml.) was added dropwise with stirring. After the addition was complete, the solution was stirred at 5°–10° C. for one hour and then poured into water. The resulting oil crystallised on standing, and the solid was filtered off and recrystallised from a mixture of ethanol and cyclohexane to give 4-acetamido-3-nitrodiphenyl sulphoxide (14 g.), m.p. 125°–130° C.

A mixture of 4-acetamido-3-nitrodiphenyl sulphoxide (11.5 g.) methanol (190 ml.) and aqueous sodium hydroxide solution (50% w/v; 30 ml.) was stirred at room temperature for 10 minutes. The mixture was then poured into water (1 liter) and extracted with dichloromethane. The extract was washed with water, dried over magnesium sulphate and evaporated, to give a yellow oil which solidified upon trituration with petrol (b.p. 60°–80° C.). The resulting solid was filtered off, to give 4-amino-3-nitrodiphenyl sulphoxide (9.1 g.), m.p. 140°–148° C.

A solution of 4-amino-3-nitrodiphenyl sulphoxide (1.0 g.) in acetone (25 ml.) was treated with methoxycarbonyl isothiocyanate (2.5 ml.) and the mixture was allowed to stand for 3 days. A further quantity of methoxycarbonyl isothiocyanate (1.0 ml.) was added and the mixture was left to stand. The solid which slowly crystallised was filtered off and recrystallised from a mixture of chloroform and methanol to give 4-(3-methoxycarbonyl-2-thioureido)-3-nitrodiphenyl sulphoxide (0.9 g.), m.p. 197°–199° C. (with decomposition).

A mixture of 4-(3-methoxycarbonyl-2-thioureido)-3-nitrodiphenyl sulphoxide (7.5 g.), methanol (1,625 ml.) and water (725 ml.) was heated to reflux. Sodium dithionite (75 g.) was added and the mixture was heated at reflux until the yellow colour had almost disappeared (about 15 minutes). The mixture was cooled and poured into water. The mixture was extracted with chloroform, the extract was dried over magnesium sulphate, and concentrated to small volume. Methanol was added to the solution which was then left to cool. The resulting solid was filtered off to give 3-amino-4-(3-methoxycarbonyl-2-thioureido)-diphenyl sulphoxide (0.5 g.), m.p. 183°–185° C.

EXAMPLE 10

A mixture of methyl chloroformate (35.5 g.), dry potassium thiocyanate (33 g.) and ethyl acetate (235 ml.) was stirred at 60° C. for 2 hours. The mixture was cooled to room temperature and filtered. The filtrate was added during 5 minutes to a solution of 4-amino-3-(2-dimethylaminoacetamido)diphenyl thioether (32 g.; prepared as hereinbefore described in Example 1) in glacial acetic acid (320 ml.) and the mixture was stirred overnight at room temperature and then poured into ice-water (700 ml.). The solution was neutralised to pH 7 by means of the addition of aqueous sodium hydroxide solution (30% w/v). The mixture was extracted with ethyl acetate (3 × 400 ml.), and the extract was dried over magnesium sulphate and evaporated to give a solid, which was recrystallised from isopropanol, to give 4-(3-methoxycarbonyl-2-thioureido)-3-(2-dimethylaminoacetamido)diphenyl thioether (37.2 g.), m.p. 145°–146° C.

By proceeding in a similar manner but replacing the 4-amino-3-(2-dimethylaminoacetamido)-diphenyl thioether used as starting material by the appropriate quantities of 4-amino-3-(2-pyrrolidin-1-ylacetamido)diphenyl thioether, 4-amino-3-(3-dimethylaminopropionamido)diphenyl thioether, 4-amino-3-(2-diethylaminoacetamido)diphenyl thioether, 4-amino-3-(2-dimethylaminoacetamido)diphenyl ether, 4-amino-3-(2-diethylaminoacetamido)diphenyl ether, and 4-amino-3-(2-dimethylaminopropionamido)diphenyl thioether, respectively, there were prepared 4-(3-methoxycarbonyl-2-thioureido)-3-(2-pyrrolidin-1-yl-acetamido)diphenyl thioether, m.p. 151°–152° C. (with decomposition), 4-(3-methoxycarbonyl-2-thioureido)-3-(3-dimethylaminopropionamido)diphenyl thioether, m.p. 148°–149° C., 3-(2-diethylaminoacetamido)-4-(3-methoxycarbonyl-2-thioureido)diphenyl thioether, m.p. 136°–137° C. (with decomposition), 4-(3-methoxycarbonyl-2-thioureido)-3-(2-dimethylaminoacetamido)diphenyl ether, m.p. 159°–161° C. (with decomposition), 3-(2-diethylaminoacetamido)-4-(3-methoxycarbonyl-2-thioureido)diphenyl ether, m.p. 175°–176° C. (with decomposition), and 4-(3-methoxycarbonyl-2-thioureido)-3-(2-dimethylamino-propionamido)diphenyl thioether, m.p. 157°–158° C. (with decomposition).

Starting materials were prepared as follows.

(a) A mixture of 4-nitro-3-(2pyrrolidin-1-ylacetamido)diphenyl thioether (14.7 g.), ethyl acetate (200 ml.), and palladium on charcoal catalyst (5g.; 5% Pd w/w) was shaken in an atmosphere of hydrogen at atmospheric pressure and room temperature until the absorption of hydrogen (about 3 litres) ceased. The mixture was then heated to reflux to dissolve some crystallised material, filtered hot to remove the catalyst, and allowed to cool to room temperature. The solid which then crystallised was filtered off to give 4-amino-3-(2-pyrrolidin-1-ylacetamido)diphenyl thioether (8.4 g.), m.p. 157°–158° C.

By proceeding in a similar manner but replacing the 4-nitro-3-(2-pyrrolidin-1-ylacetamido)-diphenyl thioether used as starting material by the appropriate quantities of 3-(3-dimethylaminopropionamido)-4-nitrodiphenyl thioether, 3-(2-diethylaminoacetamido)-4-nitrodiphenyl thioether, 3-(2-dimethylaminoacetamido)-4-nitrodiphenyl ether, 3-(2-diethylaminoacetamido)-4-nitrodiphenyl ether, and 3-(2-dimethylaminopropionamido)-4-nitrodiphenyl thioether, respectively, there were prepared 4-amino-3-(3-dimethylaminopropionamido)diphenyl thioether, m.p. 129°–130° C., 4-amino-3-(2-diethylaminoacetamido)diphenyl thioether, m.p. 76°–78° C., 4-amino-3-(2-dimethylaminoacetamido)diphenyl thioether, isolated as its dihydrochloride, m.p. 163°–165° C.

(b) (i) A stirred mixture of 3-(2-chloroacetamido)-4-nitrodiphenyl thioether (26.0 g.; prepared as described in Example 1), pyrrolidine (11.5 g.), and ethanol (200 ml.) was heated at reflux for 4 hours. The mixture was then allowed to cool, and the product which crystallised was filtered off to give 4-nitro-3-(2-pyrrolidin-1-ylacetamido)diphenyl thioether (14.7 g.), m.p. 99°–101° C.

By proceeding in a similar manner, but replacing the 3-(2-chloroacetamido)-4-nitrodiphenyl thioether and pyrrolidine used as starting materials by the appropriate quantities of 3-(3-chloropropionamido)-4-nitrodiphenyl thioether and dimethylamine, respectively, there was prepared 3-(3-dimethylaminopropionamido)-4-nitrodiphenyl thioether, m.p. 65°–67° C.

By again proceeding in a similar manner but replacing the 3-(2-chloroacetamido)-4-nitrodiphenyl thioether and pyrrolidine used as starting materials by the appropriate quantities of 3-(2-chloroacetamido)-4-nitrodiphenyl ether and dimethylamine respectively, there was prepared 3-(2-dimethylaminoacetamido-4-nitrodiphenyl ether, m.p. 119°–120° C.

(ii) A mixture of 3-(2-chloroacetamido)-4-nitrodiphenyl thioether (11.0 g.; prepared as hereinbefore described in Example 1), dry toluene (250 ml.), and diethylamine (15.5 ml.) was heated at reflux for 16 hours. The mixture was then cooled and the diethylamine hydrochloride which had crystallised was filtered off. The filtrate was evaporated to give a brown oil, which was dissolved in boiling petrol (b.p. 40°–60° C.). The solution was cooled to room temperature and the resulting crystals were filtered off to give 3-(2-diethylaminoacetamido)-4-nitrodiphenyl thioether (9.9 g.), m.p. 57°–58° C.

By proceeding in a similar manner but replacing the 3-(2-chloroacetamido)-4-nitrodiphenyl thioether used as starting material by the appropriate quantity of 3-(2-chloroacetamido)-4-nitrodiphenyl ether, there was prepared 3-(2-diethylaminoacetamido)-4-nitrodiphenyl ether, m.p. 119°–120° C.

iii. 3-(chloropropionamido)-4-nitrodiphenyl thioether (23.7 g.) was dissolved in dry toluene (100 ml.) and the solution was treated with a solution of dimethylamine in toluene (45 g.; 27% w/w). The mixture was heated on the steam bath in a pressure bottle for 16 hours. The bottle was cooled and opened, and the solution was filtered to remove dimethylamine hydrochloride. The filtrate was evaporated and the resulting yellow oil was dissolved in ethyl acetate and treated with an excess of a solution of hydrogen chloride in diethyl ether. The resulting oil solidified on scratching. This solid was filtered off to give 3-(2-dimethylaminopropionamido)-4-nitrodiphenyl thioether hydrochloride (22.4 g.), m.p. 213°–215° C.

c. A mixture of 3-amino-4-nitrodiphenyl thioether (12.3 g.), 3-chloropropionyl chloride (7.6 g.) and dry toluene (50 ml.) was heated at reflux for 1 hour. The mixture was cooled to below 80° C.; 100 ml.). The solid which precipitated was filtered off, washed with cold petrol (b.p. 60°–80° C.; 150 ml.) and dried to give 3-(3-chloropropionamido)-4-nitrodiphenyl thioether (16.1 g.), m.p. 142°–144° C.

By proceeding in a similar manner but replacing the 3-chloropropionyl chloride used as a starting material by the appropriate quantity of 2-chloropropionyl chloride there was prepared 3-(2-chloropropionamido)-4-nitrodiphenyl thioether, m.p. 58°–59° C.

By again proceeding in a similar manner, but replacing the 3-amino-4-nitrodiphenyl thioether and the 3-chloropropionyl chloride used as starting materials by the appropriate quantities chloride, there was prepared 3-(2-chloroacetamido)-4-nitrodiphenyl ether, m.p. 109°14 110° C.

d. A mixture of phenol (28.6 g.) 5-chloro-2-nitroaniline (50 g.), anhydrous potassium carbonate 45.4 g.) and dry dimethylformamide (150 ml.) was heated at reflux for 5 hours. The mixture was cooled to room temperature and then treated with water (150 ml.). The solid which precipitated was filtered off and recrystallised from isopropanol to give 3-amino-4-nitrodiphenyl ether (42.9 g.), m.p. 146°–148° C.

EXAMPLE 11

A mixture of 4-(2-benzyloxycarbonylaminoacetamido)-3-(3-methoxycarbonyl-2-thioureido)-diphenyl thioether (23.0 g.) and a solution of hydrogen bromide in glacial acetic acid (120 ml.; 40% w/w) was stirred and warmed at 40° C. for 30 minutes. The resulting suspension was poured into diethyl ether (400 ml.) and the solid which precipitated was filtered off and recrystallised from a mixture of methanol and dimethylformamide to give 4-(2-aminoacetamido)-3-(3-methoxycarbonyl-2-thioureido)diphenyl thioether hydrobromide (16.1 g.), m.p. 200°–202° C. (with decomposition).

4-(2-Aminoacetamido)-3-(3-methoxycarbonyl-2-thioureido)diphenyl thioether hydrobromide (16.1 g.) was suspended in a mixture of water (200 ml.) and chloroform (600 ml.). A solution of sodium carbonate (3.6 g.) in water (80 ml.) was added and the mixture was stirred vigorously for 20 minutes. The chloroform layer was separated, dried over magnesium sulphate and evaporated. The residual solid was crystallised from a mixture of methanol and dimethylformamide to give 4-(2-aminoacetamido)-3-(3-methoxycarbonyl-2-thioureido)diphenyl thioether (5.0 g.), m.p. 168°–170° C. (with decomposition).

4-(2-Aminoacetamido)-3-(3-methoxycarbonyl-2-thioureido)diphenyl thioether (7.0 g.) was suspended in acetone (150 ml.), and methanesulphonic acid (1.8 g.) was added with stirring. A clear solution was formed which was then treated with diethyl ether (250 ml.). A gum formed, which slowly solidified on trituration of the mixture. The solid was filtered off and recrystallised from ethanol (removing some undissolved material by filtration of the hot ethanolic solution) to give 4-(2-aminoacetamido)-3-(3-methoxycarbonyl-2-thioureido)diphenyl thioether methanesulphonate (3.9 g.), m.p. 181°–183° C. (with decomposition).

By proceeding in a similar manner but replacing the 4-(2-benzyloxycarbonylaminoacetamido)-3-(3-methoxycarbonyl-2-thioureido)diphenyl thioether used as starting material by the appropriate quantities of 4-(2-benzyloxycarbonylaminoacetamido)-3-(3-ethoxy-carbonyl-2thioureido)diphenyl thioether,
4-(2-(N-benzyloxycarbonylaminoacetamido)-4-(3-methoxycarbonyl-2thioureido)diphenyl thioether,
4-(2-benzyloxycarbonylaminoacetamido)-3-(3-methoxycarbonyl -2thioureido)-4'-methyldiphenyl thioether, 3-(2-benzyloxycarbonylaminoacetamido)-4-(3-methoxycarbonyl-2-thioureido)diphenyl ether, and
4-(2-benzyloxycarbonylaminoacetamido)-4'-chloro-3-(3-methoxycarbonyl-2-thioureido)diphenyl thioether, respectively, although in some cases without isolation of the hydrobromide salt and in some cases without the subsequent preparation of the methanesulphonate salt, there were prepared
4-(2-aminoacetamido)-3-(3-ethoxycarbonyl-2-thioureido)diphenyl thioether hydrobromide, m.p. 188°–190° C. )with decomposition),
4-(2-aminoacetamido)-3-(3-ethoxycarbonyl-2-thioureido)-diphenyl thioether, m.p. 168°–170° C. (with decomposition) 4-(2-aminoacetamido)-3-(3-ethoxycarbonyl-2-thioureido)diphenyl thioether methanesulphonate, m.p. 163°–165° C. (with decomposition),
3-(3-methoxycarbonyl-2-thioureido)-4-[2-(N-methylamino)acetamido]diphenyl thioether hydrobromide, m.p. 195°–196° C. (with decomposition),
3-(3-methoxycarbonyl-2-thioureido)-4-[2-(N-methylamino)-acetamido]diphenyl thioether, m.p. 173°–175° C. (with decomposition),
3-(2-aminoacetamido)-4-(3-methoxycarbonyl-2-thioureido)diphenyl thioether, m.p. 180°–182° C. (with decomposition), 4-(2-aminoacetamido)-3-(3-methoxycarbonyl-2-thioureido)-4'-methyldiphenyl thioether, m.p. 172°–174° C. (with decomposition),
3-(2-aminoacetamido)-4-(3-methoxycarbonyl-2-thioureido)-diphenyl ether, m.p. 180°–183° C. (with decomposition), 4-(2-aminoacetamido)-4'-chloro-3-(3-methoxycarbonyl-2-thioureido)diphenyl thioether, m.p. 170°–175° C. (with decomposition).

The starting materials were prepared as follows:- a. A stirred mixture of N-benzyloxycarbonylglycine [30 g.; prepared as described in Ber., 65, 1192, (1932)] and dry diethyl ether (190 ml.) was treated at 0° C. with phosphorus pentachloride (32 g.) during 5 minutes. The mixture was stirred at between 0° and 5° C. for a further 20 minutes and the solution was then filtered and the filtrate was evaporated. The residue was triturated with petrol (b.p. 40°–60° C.) and the petrol layer was decanted off, and this procedure was repeated several times, keeping the temperature below 20° C. throughout. A solid formed, which was filtered off to give N-benzyloxycarbonylglycyl chloride (25 g.), which was used immediately in the next stage. N-Benzyloxycarbonylglycyl chloride (13.0 g.) was added in one portion to a stirred solution of 4-amino-3-(3-methoxycarbonyl-2-thioureido)-diphenyl thioether (10.0 g.; prepared as hereinbefore described in Example 2) in dry dimethylformamide. The temperature of the mixture rose to 35° C., and the stirring was continued for 20 minutes. The solution was then poured into water. The resulting oil solidified on scratching. The solid was filtered off and recrystallised from a mixture of dimethylformamide and methanol to give 4-(2-benzyloxycarbonylaminoacetamido)-3-(3-methoxycarbonyl-2-thioureido)diphenyl thioether (13.0 g.), m.p. 184°–186° C.

By proceeding in a similar manner, but replacing the 4-amino-3-(3-methoxycarbonyl-2-thioureido)-diphenyl thioether used as a starting material by the appropriate quantities of
4-amino-3-(3-ethoxycarbonyl-2-thioureido)diphenyl thioether, 4-amino-3-(3-methoxycarbonyl-2-thioureido)-4'-methyldiphenyl thioether (prepared as hereinbefore described in Example 2),
3-amino-4-(3-methoxycarbonyl-2-thioureido)diphenyl ether (prepared as hereinbefore described in Example 2), and 4-amino-4'-chloro-3-(3-methoxycarbonyl-2-thioureido)diphenyl thioether (prepared as hereinbefore described in Example 2), respectively, there were prepared 4-(2-benzyloxycarbonylaminoacetamido)-3-(3-ethoxycarbonyl-2-thioureido)diphenyl thioether, m.p. 168°–170° C.,
4-(2-benzyloxycarbonylaminoacetamido)-3-(3-methoxycarbonyl-2-thioureido)-4'-methyldiphenyl thioether, m.p. 182°–183° C. (with decomposition),
3-(2-benzyloxycarbonylaminoacetamido)-4-(3-methoxycarbonyl-2-thioureido)diphenyl ether, m.p. 164°–168° C. (with decomposition), and
4-(2-benzyloxycarbonylaminoacetamido)-4'-chloro-3-(3-methoxycarbonyl-2-thioureido)diphenyl thioether, m.p. 187°–189° C. (with decomposition).

By again proceeding in a similar manner, but replacing the N-benzyloxycarbonylglycine used as a starting material by the appropriate quantity of N-benzyloxycarbonylsarcosine, there was prepared 4-[2-(N-benzyloxycarbonyl-N-methylamino)acetamido]-3-(3-methoxycarbonyl-2-thioureido)diphenyl thioether, m.p. 178°–180° C. (with decomposition).

A mixture of dry potassium thiocyanate (12.6 g.) acetonitrile (130 ml.) and methyl chloroformate (12.3 g.) was stirred at room temperature for 90 minutes. 4-Amino-3-(2-benzyloxycarbonylaminoacetamido)-diphenyl thioether (17.8 g.) was then added portionwise to the stirred suspension. After stirring for a further 90 minutes, the mixture was poured into water (1500 ml.) and the resulting solid was filtered off and recrystallised from a mixture of methanol and dimethylformamide to give 3-(2-benzyloxycarbonylaminoacetamido)-4-(3-methoxycarbonyl-2-thioureido)diphenyl thioether (14.4 g.), m.p. 175°–176° C. (with decomposition).

b. 4-Amino-3-(3-ethoxycarbonyl-2-thioureido)-diphenyl thioether (m.p. 168°–170° C. with decomposition) was prepared by proceeding in a manner similar to that hereinbefore described in Example 2, but replacing the methoxycarbonyl isothiocyanate used as a starting material by the appropriate quantity of ethoxycarbonyl isothiocyanate, via the intermediate 3-(3-ethoxycarbonyl-2-thioureido)-4-nitrodiphenyl thioether (m.p. 110°–112° C.).

4-Amino-3-(2-benzyloxycarbonylaminoacetamido)-diphenyl thioether was prepared as follows:-

N-Benzyloxycarbonylglycyl chloride (40.0 g.; freshly prepared as hereinbefore described) was dissolved in dry dimethylformamide (50 ml.) and the solution was added to a solution of 3-amino-4-nitrodiphenyl thioether (24.6 g.; prepared as hereinbefore described in Example 1) in dry dimethylformamide (250 ml.). The mixture was stirred for 1 hour at below 35° C. and was then poured into water (1 liter). The resulting oil solidified on scratching. The solid was filtered off and recrystalised from ethanol, to give 3-(2-benzyloxycarbonylaminoacetamido)-4-nitrodiphenyl thioether (27.7 g.), m.p. 117°–120° C.

A stirred mixture of 3-(2-benzyloxycarbonylaminoacetamido)-4-nitrodiphenyl thioether (23.3 g.), ferrous chloride tetrahydrate (3.72 g.), methanol (290 ml.) and water (64 ml.) was heated at reflux and treated with reduced iron powder (18.7 g.) during 5 minutes. The mixture was heated at reflux for one hour and then filtered while still hot. The filtrate was diluted with water (800 ml.) and the resulting solid was filtered off and recrystallised from ethanol to give 4-amino-3-(2-benzyloxycarbonylaminoacetamido)-diphenyl thioether (15.4 g.), m.p. 134°–136° C.

EXAMPLE 12

A stirred suspension of 2-amino-1-(3-methoxycarbonyl-2-thioureido)-4-thiocyanatobenzene (5.6 g.) in dichloromethane (190 ml.) was treated in one portion at room temperature with N,N-dimethylglycyl chloride hydrochloride (3.82 g.). The stirring was continued for one hour and the mixture was allowed to stand overnight. The solid was filtered off and recrystallised from ethanol to give 1-(3-methoxycarbonyl-2-thioureido)-2-(2-dimethylaminoacetamido)-4-thiocyanatobenzene hydrochloride (4.35 g.), m.p. 192°–193° C. (with decomposition).

The 2-amino-1-(3-methoxycarbonyl-2-thioureido)-4-thiocyanatobenzene, used as starting material, was prepared as follows:-

By proceeding as hereinbefore described in Example 6 but replacing the 3-amino-4'-chloro-4-nitrodiphenyl thioether used as starting material by the apropriate quantity of 2-nitro-4-thiocyanatoaniline (prepared as hereinbefore described in Example 6), there was prepared 1-(3-methoxycarbonyl-2-thioureido)-2-nitro-4-thiocyanatobenzene, m.p. 171°–172° C.

A stirred mixture of 1-(3-methoxycarbonyl-2-thioureido)-2-nitro-4-thiocyanatobenzene (27.0 g.), ferrous chloride tetrahydrate (5.85 g.), methanol (450 ml.) and water (100 ml.) was brought to reflux and treated with reduced iron powder (29.7 g.) portionwise during 5 minutes. The mixture was heated at reflux for one hour, methanol (250 ml.) was added, and the boiling solution was filtered hot. The filtrate was evaporated to dryness and the residue was extracted with boiling methanol (3 × 500 ml.). The extract was evaporated and the residue was recrystalised from methyl ethyl ketone (removing some undissolved material by filtration of the hot solution) to give 2-amino-1-(3-methoxycarbonyl-2-thioureido)-4-thiocyanatobenzene (6.5 g.), m.p. 174°–176° C. (with decomposition).

EXAMPLE 13

A suspension of 4-(2-chloroacetamido)-3-(3-methoxycarbonyl-2-thioureido)diphenyl thioether (1.0 g.) in dry toluene (20 ml.) was treated with a solution of dimethylamine in ethanol (0.9 ml.; 33% w/w), and the mixture was stirred for one hour and then allowed to stand at room temperature for 3 days. The solution was washed with water (2 × 20 ml.) and then dried over magnesium sulphate and evaporated. The residual solid was recrystallised from ethanol (removing some undissolved material by filtration of the hot solution), to give 3-(3-methoxycarbonyl-2-thioureido)-4-(2-dimethylaminoacetamido)diphenyl thioether (0.2 g.), m.p. 148°–149° C. (with decompositon).

The 4-(2-chloroacetamido)-3-(3-methoxy-carbonyl-2-thioureido)diphenyl thioether, used as starting material, was prepared as follows:

A mixture of 4-amino-3-(3-methoxycarbonyl-2-thioureido)diphenyl thioether (3.33 g.), prepared as hereinbefore described in Example 2), dry toluene (40 ml.) and chloroacetyl chloride (1.24 g.) was heated at reflux for 75 minutes. The mixture was then filtered hot and the filtrate cooled to room temperature. The resulting solid was filtered off to give 4-(2-chloroacetamido)-3-(3-methoxycarbonyl-2-thioureido(diphenyl thioether (3.15 g.), m.p. 145°–147° C. (with decomposition).

EXAMPLE 14

A stirred mixture of 4-amino-3-(3-methoxycarbonyl-2-thioureido)diphenyl thioether (2.97 g.),; prepared as hereinbefore described in Example 2), N,N-dimethylglycine hydrochloride (1.40 g.) and dichloromethane (50 ml.) was treated dropwise with phosphorus oxychloride (1.5 g.). The mixture was then stirred and heated at reflux for 8 hours and then allowed to cool. Water (50 ml.) was added with stirring and the mixture was filtered. The resulting solid was suspended in a mixture of water (100 ml.) and chloroform (100 ml.) and the stirred mixture was treated with saturated aqueous sodium bicarbonate solution until pH 8 was attained. The chloroform layer was separated, dried over magnesium sulphate and evaporated to give a residual solid, which was recrystalised from isopropanol to give 3-(3-methoxycarbonyl-2-thioureido)-4-(2-dimethylaminoacetamido)-diphenyl thioether (1.5 g.), m.p. 147°–148° C. (with decomposition).

EXAMPLE 15

A solution of 4-(3-methoxycarbonyl-2-thioureido)-3-(2-dimethylaminoacetamido)diphenyl thioether (2.0 g.; prepared as hereinbefore described in Example 1) in acetone (100 ml.) was treated with methyl iodide (0.71 g.). The flask was closed and allowed to stand for 4 days. An excess of diethyl ether was then added and the solvents were decanted from the gum which separated. The gum was triturated with a further quantity of diethyl ether (80 ml.) to give a solid, which was recrystallised from ethanol to give 4-(3-methoxycarbonyl-2-thioureido)-3-(2-trimethylammonioacetylamino)diphenyl thioether iodide (0.7 g.), m.p. 162°–164° C. (was decomposition).

EXAMPLE 16

A stirred mixture of dry potassium thiocyanate (10.3 g.) and ethyl acetate (75 ml.) was heated to 60° C. and treated with isobutyl chloroformate (14.6 g.) dropwise during 5 minutes. The mixture was stirred for 2 hours at 60° C., and then cooled and filtered. The filtrate was added in one portion to a solution of 4-amino-3-(2-dimethylaminoacetamido)diphenyl thioether (10.0 g.; prepared as hereinbefore described in Example 1) in glacial acetic acid (100 ml.) at room temperature. The mixture was stirred for 4 hours and then allowed to stand overnight. The reaction mixture was poured into water (300 ml.) and neutralised by treatment with aqueous sodium hydroxide solution (30% w/v). The solution was extracted with ethyl acetate (2 × 100 ml.) and the extract was dried over magnesium sulphate and evaporated. The resulting oil was dissolved in diethyl ether (200 ml.) and treated with an excess of a solution of hydrogen chloride in diethyl ether. The solid which formed was recrystallised from ispropanol and then suspended in water (250 ml.). The suspension was made alkaline by the addition of an excess of sodium carbonate, and was then extracted with chloroform. Evaporation of the chloroform extract gave 3-(2-dimethylaminoacetamido)-4-[3-(2-methylpropoxycarbonyl)-2-thioureido]diphenyl thioether (3.1 g.), m.p. 104°–107° C.

By proceeding in a similar manner but replacing the isobutyl chloroformate used as a starting material by the appropriate quantity of n-butyl chloroformate, there was prepared 4-(3-n-butoxycarbonyl-2-thioureido)-3-(2-dimethylaminoacetamido)diphenyl thioether, m.p. 115°–116° C. (with decomposition).

EXAMPLE 17

By proceeding in a manner similar to that hereinbefore described in Example 10 but replacing the pyrrolidine used as a starting material by the appropriate quantity of morpholine, there was prepared 4-(3-methoxycarbonyl-2-thioureido)-3-(2-morpholinoacetamido)diphenyl thioether, m.p. 183° C. (with decomposition), via the intermediates 3-(2-morpholinoacetamido)-4-nitrodiphenyl thioether, m.p. 169°–171° C., and 4-amino-3-(2-morpholinoacetamido)diphenyl thioether, m.p. 128°–130° C.

EXAMPLE 18

By proceeding in a manner similar to that hereinbefore described in Example 10 but replacing the pyrrolidine used as a starting material by the appropriate quantity of di-n-propylamine, there was prepared 4-(3-methoxycarbonyl-2-thioureido)-3-(2-di-n-propylaminoacetamido)diphenyl thioether, m.p. 133°–135° C. (with decomposition), via the intermediates 4-nitro-3-(2-di-n-propylaminoacetamido)diphenyl thioether (isolated as the hydrochloride salt, m.p. 125°–126° C.), and 4-amino-3-(2-di-n-propylaminoacetamido)diphenyl thioether (isolated as the dihydrochloride salt, m.p. 185°–187° C.).

EXAMPLE 19

By proceeding in a manner similar to that hereinbefore described in Example 10 but replacing the 4-amino-3-(2-dimethylaminoacetamido)diphenyl thioether and methyl chloroformate used as starting materials by the appropriate quantities of 2-(2-dimethylaminoacetamido)-4-methylsulphonyl-aniline and ethyl chloroformate, respectively, there was prepared 2-(3-ethoxycarbonyl-2-thioureido)-1-(2-dimethylaminoacetamido)-4-methylsulphonyl-benzene (isolated as the hydrochloride salt, m.p. 196°–198° C.).

2-(2-Dimethylaminoacetamido)-4-methylsulphonyl-aniline, used as a starting material, was prepared as follows:

a. By proceeding in a manner similar to that hereinbefore described in Example 10(a) but replacing the 4-nitro-3-(2-pyrrolidin-1-ylacetamido)diphenyl thioether used as starting material by the appropriate quantity of 2-(2-dimethylaminoacetamido)-4-methylsulphonyl-1-nitrobenzene, there was prepared 2-(2-dimethylaminoacetamido)-4-methylsulphonyl-aniline, m.p. 130°–132° C.

b. By proceeding in a manner similar to that hereinbefore described in Example 10(b)(i) but replacing the 3-(2-chloroacetamido)-4-nitrodiphenyl thioether and pyrrolidine used as starting materials by the appropriate quantities of 2-(2-bromoacetamido)-4-methylsulphonyl-1-nitrobenzene and dimethylamine, respectively, there was prepared 2-(2-dimethylaminoacetamido)-4-methylsulphonyl-1-nitrobenzene, m.p. 166°–168° C.

c. By proceeding in a manner similar to that hereinbefore described in Example 10(c), but replacing the 3-amino-4-nitrodiphenyl thioether and the 3-chloropropionyl chloride used as starting materials by the appropriate quantities of 4-methylsulphonyl-2-nitroaniline and bromoacetyl bromide, respectively, there was prepared 2-(2-bromoacetamido)-4-methylsulphonyl-1-nitrobenzene, m.p. 155°–158° C. (with decomposition).

d. 2-Chloro-4-methylsulphonyl-1-nitrobenzene (73 g.; prepared according to the method described in French Patent Specification No. 1509499), ethanol (400 ml.) and ammonia (44 g.) were heated together at 120° C. in a pressure vessel for 8 hours. The vessel was then cooled and opened and the solid was filtered off and recrystallised from ethanol to give 4-methylsulphonyl-2-nitroaniline (19.0 g.), m.p. 195°–198° C.

EXAMPLE 20

By proceeding in a manner similar to that hereinbefore described in Example 2 but replacing the 4-amino-3-(3-methoxycarbonyl-2-thioureido)diphenyl thioether used as starting material by the appropriate quantity of 2-amino-4-[2-(ethylthio)ethoxy]-1-(3-methoxycarbonyl-2-thioureido)benzene, there was prepared 4-[2-(ethylthio)ethoxy]-1-(3-methoxycarbonyl-2-thioureido)-2-(2-dimethylaminoacetamido)benzene, m.p. 112°–113° C. (with decomposition).

The 2-amino-4-[2-(ethylthio)ethoxy]-1-(3-methoxycarbonyl-2-thioureido)benzene used as starting material was prepared as follows:

By proceeding in a manner similar to that hereinbefore described in Example 2 but replacing the 3-(3-methoxycarbonyl-2-thioureido)-4-nitrodiphenyl thioether used as starting material by the appropriate quantity of 4-[2-(ethylthio)ethoxy]-1-(3-methoxycarbonyl-2-thioureido)-2-nitrobenzene, there was prepared 2-amino-4-[2-(ethylthio)ethoxy]-1-(3-methoxycarbonyl-2-thioureido)benzene, m.p. 135°–136° C.

By proceeding in a manner similar to that hereinbefore described in Example 6(b) but replacing the 3-amino-4'-chloro-4-nitrodiphenyl thioether used as starting material by the appropriate quantity of 4-[2-(ethylthio)ethoxy]-2-nitroaniline, there was prepared 4-[2-(ethylthio)ethoxy]-1-(3-methoxycarbonyl-2-thioureido)-2-nitrobenzene; m.p. 115°–117° C.

A solution of 4-amino-3-nitrophenol (17.5 g.) in ethanol (300 ml.) was treated with solid potassium hydroxide (6.38 g.). The mixture was treated with a solution of 2-bromoethyl ethyl thioether (21.2 g.) in ethanol (100 ml.), and stirred at room temperature for 4 hours. The reaction mixture was then concentrated in vacuo and the residue was dissolved in chloroform (200 ml.). The chloroform solution was washed with aqueous sodium bicarbonate solution (10% w/v; 200 ml.), dried over magnesium sulphate and evaporated to give 4-[2-(ethylthio)ethoxy]-2-nitroaniline (23.4 g.) in the form of a dark red oil, which was used in the next stage without further purification being necessary.

The compounds of general formula I are conveniently administered as anthelmintic agents in the form of compositions in a unit dosage form, and the present invention includes within its scope therapeutically-useful, more especially veterinary, compositions which comprise, as active ingredient, at least one benzene derivative of formula I in association with a significant amount of one or more compatible and pharmaceutically-acceptable carriers or adjuvants. The invention includes especially such compositions made up for oral administration, for example a tablet, pill, capsule or bolus, or more particularly, a paste, gel or drench.

Solid compositions for oral administration include compressed tablets, pills, boluses and granules, which may optionally be coated with a pharmaceutically acceptable alkali-stable or acid-stable material (e.g. an enteric coating) and dispersible powders. In such solid compositions one or more of the active compounds is or are admixed with at least one inert diluent such as potato starch, alginic acid, sucrose, lactose, or a resin. The compositions may also comprise, as is normal practice, additional substances other than inert diluents, e.g. lubricating agents such as magnesium stearate. Semi-solid compositions for oral administration include pastes and gels containing the active substance and a suitable inert diluent such as polyethylene glycol (6000). Liquid compositions for oral administration include pharmaceutically acceptable emulsions, solutions, suspensions, syrups and elixirs containing inert diluents commonly used in the art, such as water and liquid paraffin. Besides inert diluents such compositions may also comprise compatible adjuvants such as wetting, suspending and emulsifying agents and stabilising, thickening, perfuming, sweetening and flavouring agents. The compositions according to the invention for oral administration also include capsules of absorbable material such as gelatin containing one or more of the active substances with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, preserving, wetting, emulsifying and dispersing agents. They may be sterilised, for example, by filtration through a bacteria-retaining filter, by incorporation in the compositions of sterilising agents, or by heating. They may also be manufactured in the form of sterile solid compositions, which can be dissolved in sterile water or some other sterile injectable medium immediately before use.

The percentage of the benzene derivatives of formula I in the above compositions may be varied, it being necessary that it should constitute a proportion such that a suitable dosage for the therapeutic effect desired shall be obtained. In general, compositions containing from about 5% to about 90% by weight of active ingredient are satisfactory.

The compounds of general formula I may also be conveniently administered as anthelmintics by dermal application and absorption through the skin of the animal and the present invention includes within its scope liquid therapeutically-useful, more especially veterinary, compositions suitable for dermal administration which comprise, as active ingredient, at least one benzene derivative of formula I in association with a significant amount of a liquid pharmaceutically acceptable carrier suitable for dermal application. Compositions for dermal administration according to the present invention preferably comprise a solution of at least one benzene derivative of general formula I in a liquid pharmaceutically-acceptable solvent, for example, a hydrocarbon, e.g. xylene, toluene, benzene or a mixture of aromatic hydrocarbons whose boiling point is between 130° C and 250° C, e.g. between 180° C and 220° C, or paraffins containing from 6 to 20 carbon atoms, halogenated hydrocarbons, e.g. carbon tetrachloride, ketones, e.g. cyclohexanone or butanone, esters, e.g. ethyl acetate, ethyl benzoate or glyceryl triacetate, ethers, e.g. diisopropyl ether or tetrahydrofuran, alcohols, e.g. alkanols containing from 2 to 8 carbon atoms (e.g. butanol, isopropanol or amyl alcohol) or glycols (e.g. propylene glycol), amides, e.g. lower alkyl amides (e.g. dimethylformamide), sulphones, e.g. lower dialkyl sulphones (e.g. dimethyl sulphone) or sulpholane, or sulphoxides, e.g. lower dialkyl sulphoxides (e.g. dimethyl sulphoxide) or mixtures of such solvents. Preferred carriers for compositions suitable for dermal application are amyl alcohol and dimethyl sulphoxide and mixtures thereof. Liquid compositions suitable for dermal application preferably contain a thickening agent in order to reduce run-off of the liquid composition from the skin of the animal, thereby facilitating absorption of the active ingredient through the skin of the animal. Suitable thickening agents are, for example, soaps, fats and waxes, e.g. lanolin, mineral or vegetable oils and polymers, e.g. polyisobutylene. Liquid compositions suitable for dermal application may also contain systemic insecticides known to be suitable for dermal administration to animals, e.g. phosalone, and bitter aloes, which inhibits licking of the treated skin by other animals. The liquid compositions for dermal administration may be applied to the skin of the animal by conventional techniques, e.g. dipping, spraying and pouring over the back of the animal. The percentage of the benzene derivative of formula I in the liquid compositions suitable for dermal application may be varied, it being necessary that it should constitute a proportion such that a suitable dosage for the therapeutic effect desired is obtained. Preferably, the liquid compositions suitable for dermal administration contain from 1% to 10% weight/volume of the benzene derivative of formula I, from 45% to 95% volume/volume of liquid pharmaceutically-acceptable carrier and from 5% to 50% weight/volume of thickening agent and/or systemic insecticide.

For therapeutic purposes, particularly when continuous administration over a period is desired, the compounds of general formula I may be administered dissolved in, dispersed in, or mixed with, animal feedstuffs, drinking water and other liquids normally consumed by the animals, or in compositions containing the benzene derivatives dispersed in or mixed with any other suitable inert physiologically innocuous carrier or diluent which is orally administrable. By the term 'inert physiologically innocuous carrier or diluent' is meant a carrier or diluent which is substantially non-reactive with the active ingredient and is not harmful to the animals on oral administration. Such compositions may be administered in the form of powders, pellets, feed blocks, licks, solutions, suspensions and emulsions, to the animals to supply the desired dosage of the benzene derivatives or used as concentrates or supplements to be diluted with additional carrier, feedstuff, drinking water or other liquids normally consumed by the animals, before administration. Suitable inert physiologically innocuous carriers or diluents include cereals, e.g.

wheat flour or meal, maize gluten, lactose, glucose, sucrose, molasses, talc, kaolin, calcium phosphate, potassium sulphate, sodium chloride, urea and diatomaceous earths such as kieselguhr. Concentrates or supplements intended for incorporation into drinking water or other liquids normally consumed by the animals to give solutions, emulsions or stable suspensions, may also comprise the active ingredient in association with a surface-active wetting, dispersing or emulsifying agent such as Teepol, polyoxyethylene(20)sorbitan mono-oleate or the condensation product of β-naphthalenesulphonic acid with formaldehyde, with or without a physiologically innocuous, preferably water-soluble, carrier or diluent, for example, sucrose, glucose or an inorganic salt such as potassium sulphate, or concentrates or supplements in the form of stable dispersions or solutions obtained by mixing the aforesaid concentrates or supplements with water or some other suitable physiologically innocuous inert liquid carrier or diluent, or mixtures thereof.

The compositions described above may be prepared by mixing the benzene derivatives of formula I with the inert physiologically innocuous carriers or diluents in any manner known to the art. Solid compositions are conveniently prepared by intimately mixing or dispersing the benzene derivatives uniformly throughout the feedstuffs or other solid carrier or diluent by methods such as grinding, stirring, milling or tumbling or by dissolving the benzene derivatives in a solvent, e.g. water or a suitable organic solvent, dispersing the solution so obtained in the feedstuff or other solid carrier or diluent and removing the solvent by any means known to the art. Medicated feedstuffs may also be prepared by mixing in concentrates or supplements containing higher concentrates of active ingredient to give feedstuffs throughout which the benzene derivatives are uniformly distributed at the desired concentration. The desired concentration of active ingredient in the compositions of the present invention is obtained by the selection of an appropriate ratio of the benzene derivatives to carrier or diluent.

Medicated feedstuffs will normally contain between 0.001% and 3% by weight of the benzene derivatives of formula I to give the required dosage. Concentrates and supplements will normally contain between 0.02% and 90%, preferably 0.1% to 50%, by weight of the benzene derivatives being, if desired, suitably diluted as hereinbefore described to give the required dosage.

Medicated animal feedstuffs, drinking water and other liquids normally consumed by the animals and compositions containing the benzene derivatives of formula I dispersed in, or admixed with, any other suitable inert carrier or diluent, as hereinbefore described, including concentrates or supplements, form further features of the present invention.

Anthelmintic compositions according to the present invention may also contain bacteriostats, bactericidal agents, sporicidal agents and pharmaceutically acceptable colouring agents. The compositions may also contain, if desired, auxiliary therapeutic agents, for example fluke drugs such as 4-cyano-2-iodo-6-nitrophenol, hexachloroethane, carbon tetrachloride, 3,3',5,5',6,6'-hexachloro-2,2'-dihydroxydiphenylmethane, 2,2'-dihydroxy-3,3',5,5',6-pentachlorodiphenylmethane, 2,2'-dihydroxy-3,3',5,5',6-pentachlorobenzanilide, 2,2'-dihydroxy-3,3'-dinitro-5,5'-dichlorodiphenyl, bis[2-(4-acetamidophenoxy)ethyl] ether or 2-acetoxy-4'-chloro-3,5-diiodobenzanilide, 2-(4-thiazolyl)benzimidazole, 5(6)-isopropoxycarbonylamino-2-(4-thiazolyl)benzimidazole, methyl 5(6)-butyl-2-benzimidazolecarbamate, methyl 5(6)-benzoyl-2-benzimidazolecarbamate, 6-phenyl-2,3,5,6-tetrahydroimidazo[2,1-b]thiazole, trans-1,4,5,6-tetrahydro-1-methyl-2-(2-thien-2'-ylvinyl)pyrimidine, phenothiazine, cyanacethydrazide piperazine and its salts such as piperazine adipate, 1-diethylcarbamoyl-4-methylpiperazine, tetrachloroethylene, 4,4'-dichloro-2,2'-dihydroxydiphenyl-methane, N-(2-chloro-4-nitrophenyl)-5-chlorosalicylamide, N,N-dibutyl-4-hexyloxynaphthamide, trans-1,4-bis-(2-isothiocyanatoethyl)cyclohexane and 1-styrylpyridinium salts, e.g. the bromide, embonate, amsonate or isethionate.

The new compounds of general formula I may be used as fungicides against fungi pathogenic to growing plants, seeds and fruits in the form of fungicidal compositions, suitable for use in agriculture, containing as active ingredient at least one of the benzene derivatives of general formula I in association with one or more diluents compatible with the benzene derivatives and suitable for use in fungicidal compositions. Preferably the compositions contain between 0.005% and 95% by weight of the compounds of general formula I. Suitable solid diluents include aluminum silicate, kieselguhr, tricalcium phosphate, powdered cork, adsorbent carbon black, magnesium silicate, a clay such as kaolin, bentonite or attapulgite or a compatible solid wetting, dispersing or emulsifying agent. The compositions containing solid diluents, which may take the form of dusts or wettable powders, are prepared by impregnating the solid diluents with solutions of the compounds of general formula I in volatile solvents and evaporating the solvents, or by injecting those compounds of general formula I which are viscous liquids at room temperature, under high pressure into a suitable powder-blender containing the solid diluent or diluents, and, if necessary, grinding the product so as to obtain powders.

The wetting, dispersing and emulsifying agents which may be present, particularly in wettable powders, may be of the ionic or non-ionic types, for example, sulphoricinoleates, quaternary ammonium derivatives or products based upon condensates of ethylene oxide with nonyl and octyl phenol, or fatty acid esters of anhydrosorbitols which have been rendered soluble by etherification of the free hydroxy groups by condensation with ethylene oxide, or mixtures of these types of agents. Wettable powders according to the present invention may be treated with water immediately before use to give suspensions ready for application.

Liquid compositions may take the form of solutions, suspensions, slurries and emulsions of the compounds of general formula I which may, if desired, incorporate wetting, dispersing or emulsifying agents. These emulsions, suspensions and solutions may be prepared using aqueous, organic or aqueous-organic diluents, for example acetophenone, isophorone, toluene, xylene and mineral, animal or vegetable oils (and mixtures of these diluents), which may contain wetting, dispersing or emulsifying agents of the ionic or non-ionic types or mixtures thereof, for example those of the types described above. When desired, the emulsions containing the compounds of general formula I may be used in the form of self-emulsifying concentrates containing the active substances dissolved in the emulsifying agents or in solvents containing emulsifying agents compatible with the active substance, the simple addition of water to such concentrates producing compositions ready for use. Fungicidal compositions in the form of aerosols containing the compounds of general formula I are also within the scope of the present invention. If desired, the fungicidal compositions according to the present invention may contain other adjuvants such as adhesives.

Agricultural compositions according to the present invention may also contain, as well as the compound or compounds of formula I, pesticides such as insecticides, for example γ-1,2,3,4,5,6-hexachlorocyclohexane, or other fungicides, for example 3a,4,7,7a-tetrahydro-N-(trichloromethanesulphenyl)phthalimide.

Accordingly, there is provided a method for the destruction of fungi pathogenic to plants which comprises the application of the fungicidal compositions comprising compounds of formula I, if necessary after suitable dilution, to crop-growing areas infested with these fungi. By the term 'crop-growing areas' is meant areas in which economically valuable crops are growing. Preferably the fungicidal compositions are applied at rates of from 0.25 to 3 lbs. of benzene derivative per acre, more particularly in the form of aqueous sprays prepared by diluting concentrates with water.

There is further provided a method for the protection of seeds against fungi which comprises the treatment of the seeds with the fungicidal compositions comprising compounds of formula I, if necessary after dilution. Preferably the fungicidal compositions are applied to the seeds at rates of from 0.05% to 0.2% of benzene derivative, more particularly in the form of dry powder or slurry compositions.

There is further provided a method for the protection from fungi of fruits after harvest which comprises the treatment of the fruits with the fungicidal compositions comprising compounds of formula I, if necessary after dilution. Preferably the fungicidal compositions are applied to the fruits at rates of from 0.25 to 3.0 lbs of benzene derivative per 100 gallons of water, more particularly in the form of a solution in which the fruits are dipped.

The new compounds of general formula I may be used as fungicides against fungi pathogenic to animals in the form of therapeutically useful compositions comprising at least one of the compounds in association with a pharmaceutically-acceptable carrier or coating of the type hereinbefore described as suitable for the use of compounds of general formula I as anthelmintics. Therapeutically useful compositions comprising at least one of the new compounds of general formula I for use against fungi pathogenic to animals may be formulations suitable for topical application, e.g. lotions, ointments or creams.

The following Examples illustrate the formulation of therapeutically useful and fungicidal compositions including benzene derivatives of formula I.

It is to be understood that, in each of the following Examples and unless otherwise specified, any other compound of formula I may be substituted for the compound specifically mentioned, bearing in mind that the proportions of the ingredients and methods of preparing the compositions may be modified in accordance with the physicochemical properties of the compound of formula I used, such modification being readily carried out after simple experimentation by one skilled in the art of formulating therapeutically useful or fungicidal compositions.

EXAMPLE 21

Tablets of the formula:

| | |
|---|---|
| 4-(3-methoxycarbonyl-2-thioureido)-3-(2-dimethylaminoacetamido)diphenyl thioether | 250 mg. |
| lactose | 200 mg. |
| starch | 50 mg. |
| polyoxyethylene sorbitan monolaurate | 0.5 mg. |
| magnesium stearate | 5 mg. | were prepared by mixing the benzene derivative and the lactose with part of the starch and granulating with a 5% starch mucilage containing the polyoxyethylene sorbitan monolaurate.

The mixture was sifted through a 20 mesh British Standard sieve, dried, and the remainder of the starch, together with the magnesium stearate, was incorporated into the mixture. After a second sifting through a 20 mesh British Standard sieve the mixture was compressed into tablets.

EXAMPLE 22

A wettable powder was made up from the following components:

| | |
|---|---|
| 4-(3-methoxycarbonyl-2-thioureido)-3-(2-dimethylaminoacetamido)diphenyl thioether | 75% w/w |
| diatomaceous earth | 15% w/w |
| micronised silica | 2% w/w |
| wetting agent (blend of polyoxyethylene alkyl ethers, polyoxyethylene fatty acids and their esters) | 8% w/w | by mixing the components and milling them in an air-jet miller.

EXAMPLE 23

A wettable powder was made up from the following components:

| | |
|---|---|
| 4-(3-methoxycarbonyl-2-thioureido)-3-(2-dimethylaminoacetamido)diphenyl thioether | 52% w/w |
| finely-divided synthetic magnesium silicate | 39% w/w |
| micronised silica | 2% w/w |
| wetting agent (blend of polyoxyethylene alkyl ethers, polyoxyethylene fatty acids and their esters) | 7% w/w | by mixing the components and milling them in an air-jet miller.

EXAMPLE 24

4-(3-Methoxycarbonyl-2-thioureido)-3-(2-dimethylaminoacetamido)diphenyl thioether (1 g.), previously sifted through a 40 mesh British Standard sieve, was packed into a gelatin capsule.

EXAMPLE 25

A preparation for oral administration was obtained by mixing 4-(3-methoxycarbonyl-2-thioureido)-3-(2-dimethyl-aminoacetamido)diphenyl thioether (1 g.), previously sifted through a 40 mesh British Standard sieve, and polyethylene glycol 6000 (10 g.) at 50° C, and cooling to 25° C to obtain a gel.

EXAMPLE 26

4-(3-Methoxycarbonyl-2-thioureido)-3-(2-dimethylaminoacetamido)diphenyl thioether (18 parts w/w)

was added to wheat middlings (82 parts w/w) and intimately mixed to give a concentrate suitable for incorporation in an animal feedstuff at a rate sufficient to give an anthelmintically-effective amount of the benzene derivative in the feedstuff consumed by the animal.

EXAMPLE 27

4-(3-Methoxycarbonyl-2-thioureido)-3-(2-dimethylaminoacetamido)diphenyl thioether (5 parts by weight) was added to limestone flour (20 parts w/w). The mixture was ground to give a concentrate suitable for incorporation in an animal feedstuff at a rate sufficient to give an anthelmintically-effective amount of the benzene derivative in the feedstuff consumed by the animal.

EXAMPLE 28

A suspension for oral administration for use as an anthelmintic was obtained by mixing diethylcarbamazine citrate (4.4 g; prepared as described in United States Patent No. 2,467,895) and 4-(3-methoxycarbonyl-2-thioureido)-3-(2-dimethylaminoacetamido)-diphenyl thioether (19.6 g. of a 52% w/w wettable powder prepared as described in Example 23) with water (140 ml.).

EXAMPLE 29

A suspension for oral administration for use as an anthelmintic was obtained by mixing 1-styryl-pyridinium amsonate monohydrate (10 g; prepared as described in British Pat. No. 1,221,061), previously sifted through a 60 mesh British Standard sieve, and 4-(3-methoxycarbonyl-2-thioureido)-3-(2-dimethylaminoacetamido)diphenyl thioether, (19.6 g. of a 52% w/w wettable powder prepared as described in Example 23) with water (140 ml.).

EXAMPLE 30

A solution for oral administration as an anthelmintic was obtained by dissolving 4-(3-methoxycarbonyl-2-thioureido)-3-(2-dimethylaminoacetamido)diphenyl thioether methanesulphonate (10 g.) and 1-styryl-pyridinium isethionate (10 g.) in water (100 ml.). This solution was sterilised by filtration through a bacteria-retaining filter to give a sterile composition suitable for parenteral administration as an anthelmintic.

EXAMPLE 31

A solution for oral administration as an anthelmintic was obtained by dissolving diethylcarbamazine citrate (4.4 g.) and 4-(3-methoxycarbonyl-2-thioureido)-3-(2-dimethylaminoacetamido)diphenyl thioether methanesulphonate (10 g.) in water (100 ml.). This solution was sterilised by filtration through a bacteria-retaining filter to give a sterile composition suitable for parenteral administration as an anthelmintic.

EXAMPLE 32

A wettable powder was obtained by mixing:

| | |
|---|---|
| 4-(3-methoxycarbonyl-2-thioureido)-3-(2-dimethylaminoacetamido)diphenyl thioether hydrochloride | 50 parts w/w |
| Texofor FX 500 (an alkylphenol-polyoxyethylene condensate) | 10 parts w/w |
| Celite 281 (a finely-divided diatomaceous earth) in a ribbon-blender. | 40 parts w/w |

EXAMPLE 33

A wettable powder was obtained by mixing:

| | |
|---|---|
| 4-(3-methoxycarbonyl-2-thioureido)-3-(2-dimethylaminoacetamido)diphenyl thioether hydrochloride | 50 parts w/w |
| Belloid TD (a polymethyl bis-naphthyl sodium sulphonate) | 10 parts w/w |
| Clarcelflo SAS (an expanded pearlite | 35 parts w/w |
| Aerosil (a finely-divided silicon dioxide) in a ribbon-blender. | 5 parts w/w |

EXAMPLE 34

A liquid concentrate in the form of a suspension was obtained by mixing:

| | |
|---|---|
| 4-(3-methoxycarbonyl-2-thioureido)-3-(2-dimethylaminoacetamido)diphenyl thioether hydrochloride | 60 parts w/w |
| bentonite | 3 parts w/w |
| Cutafor 09 (a polyethoxylated alkylamine) | 10 parts w/w |
| white spirit (a petroleum distillate) | 10 parts w/w |

EXAMPLE 35

4-(3-Methoxycarbonyl-2-thioureido)-3-(2-dimethylaminoacetamido)diphenyl thioether (10 g.) was dissolved in dimethyl sulphoxide (100 ml.) to give a solution suitable for dermal or parenteral administration.

EXAMPLE 36

A mineral lick was prepared in the usual manner from

| | |
|---|---|
| 4-(3-methoxycarbonyl-2-thioureido)-3-(2-dimethylaminoacetamido)diphenyl thioether | 2 parts w/w |
| sodium chloride | 195 parts w/w |
| other minerals (e.g. magnesium compounds and phosphorus compounds) and vitamins known to be desirable in the diet of animals. | 3 parts w/w |

EXAMPLE 37

A liquid food supplement was prepared from

| | |
|---|---|
| 4-(3-methoxycarbonyl-2-thioureido)-3-(2-dimethylaminoacetamido)diphenyl thioether | 1 part w/w |
| molasses | 650 parts w/w |
| water | 349 parts w/w |

EXAMPLE 38

Drinking water was treated so as to render it suitable for continuous medication of animals by dissolving therein 4-(3-methoxycarbonyl-2-thioureido)-3-(2-dimethylaminoacetamido)diphenyl thioether hydrochloride (0.01% w/w).

EXAMPLE 39

A solution for oral administration as an anthelmintic was obtained by dissolving 4-(3-methoxycarbonyl-2-thioureido)-3-(2-dimethylaminoacetamido)diphenyl thioether methanesulphonate (10 g.) in water (100 ml.).

This solution was sterilised by filtration through a bacteria-retaining filter to give a sterile composition

EXAMPLE 40

4-(3-Methoxycarbonyl-2-thioureido)-3-(2-dimethylaminoacetamido)diphenyl thioether (250 parts w/w) was combined with Atlox 4855 (6 parts w/w) and Aerosil 200 (1 part w/w) and water (to 500 parts w/w) and the mixture was passed through a colloid mill, to give a slurry suitable for use as a seed-dressing.

Atlox 4855 is a polyoxyethylene triglyceride/alkyl aryl sulphonate blend and Aerosil 200 is microfine silicon dioxide.

EXAMPLE 41

4-(3-Methoxycarbonyl-2-thioureido)-3-(2-dimethylaminoacetamido)diphenyl thioether hydrochloride (0.4 lb.) was dissolved in water (100 gallons) to form a solution suitable for use as a post-harvest dip for fruits.

We claim:

1. A benzene derivative of the formula:

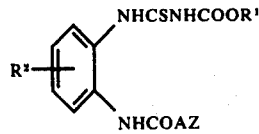

I wherein $R^1$ represents alkyl of 1 to 4 carbon atoms, $R^2$ represents a group selected from $-SR^3$, $-SOR^3$, $-SO_2R^3$, $-OR^3$, $-SCONH_2$, and $-T(CH_2)_mT^1R^4$, wherein $R^3$ represents alkyl of 1 to 6 carbon atoms, cycloalkyl of 3 to 7 carbon atoms, alkenyl or alkynyl of 3 to 6 carbon atoms, aralkyl with 1 or 2 carbon atoms in the alkyl moiety, or $R^3$ represents an aryl group or an aryl group substituted by a halogen atom or an alkyl or alkoxy group of 1 to 3 carbon atoms, or represents cycloalkylalkyl in which the cycloalkyl moiety contains from 3 to 7 carbon atoms and the alkyl moiety contains 1 or 2 carbon atoms, $R^4$ represents hydrogen, alkyl of 1 to 4 carbon atoms, T and $T^1$ each represent oxygen, sulphur or sulphinyl, and m is an integer from 1 to 7 inclusive whose position on the benzene ring is either para to the group -NHCSNHCOOR$^1$ or para to the group $-NHCOAZ$, A represents a bivalent straight-chain aliphatic hydrocarbon radical of 1 to 4 carbon atoms or a said hydrocarbon radical substituted by at least one methyl group, and Z represents a group of the formula:

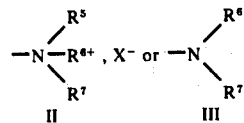

wherein $R^5$ represents hydrogen, alkyl of 1 to 4 carbon atoms, $R^6$ represents hydrogen, alkyl of 1 to 4 carbon atoms, or phenylalkyl with 1 to 2 carbon atoms in the alkyl moiety, and $R^7$ represents hydrogen or alkyl of 1 to 4 carbon atoms, and $X^-$ represents a pharmaceutically acceptable or agriculturally acceptable anion.

2. A benzene derivative according to claim 1 wherein $R^2$ represents a group selected from $-SR^3$, $-SOR^3$, $-SO_2R^3$, $-OR^3$, $-SCONH_2$ and $T(CH_2)_mT^1R^4$, wherein $R^3$ represents alkyl of 1 to 6 carbon atoms, cycloalkyl of 3 to 7 carbon atoms, alkenyl or alkynyl of 3 to 6 carbon atoms, aralkyl with 1 or 2 carbon atoms in the alkyl moiety, or an aryl group, and $R^1$, $R^4$, T, $T^1$ and m are as defined in claim 1.

3. A benzene derivative according to claim 1 wherein Z represents a group of formula II as depicted in claim 1 and $X^-$ represents a pharmaceutically acceptable anion.

4. A benzene derivative according to claim 3 wherein $X^-$ represents a chloride or methanesulphonate ion.

5. A benzene derivative according to claim 1 wherein $R^1$ represents methyl, $R^2$ represents a group selected from $-SR^3$, $-SOR^3$ and $-OR^3$ wherein $R^3$ is alkyl of 2 to 4 carbon atoms, cycloalkyl of 3 to 7 carbon atoms, benzyl or phenyl, A represents methylene, ethylene or ethylidene and Z represents a group of formula II or III as depicted in claim 1 wherein $R^6$ and $R^7$ represent hydrogen, alkyl of 1 to 3 carbon atoms, and in formula II (when present), $R^5$ represents hydrogen and $X^-$ represents a halide ion or a methanesulphonate ion.

6. A benzene derivative according to claim 1 wherein $R^1$ represents methyl, $R^2$ represents phenylthio or cyclopentylthio, A represents methylene, ethylene or ethylidene, and Z represents a group of formula II or III as depicted in claim 1 wherein $R^6$ and $R^7$ each represent methyl, and, in formula II (when present), $R^5$ represents hydrogen and $X^-$ represents a chloride or methanesulphonate ion.

7. A benzene derivative according to claim 1 wherein $R^1$ represents methyl or ethyl, $R^2$ represents phenylthio and Z represents a group of formula II as depicted in claim 1 wherein $R^5$, $R^6$ and $R^7$ each represent hydrogen or methyl and $X^-$ represents a halide ion or a methanesulphonate ion, or Z represents a group of formula III wherein $R^6$ and $R^7$ each represent hydrogen or methyl.

8. A benzene derivative according to claim 5 wherein $X^-$ represents a chloride ion.

9. A benzene derivative according to claim 7 wherein $X^-$ represents a chloride ion.

10. Method for the treatment of helminth infections in man and domestic animals which comprises administering to man or a domestic animal infected with helminths an anthelmintically effective amount of at least one benzene derivative as claimed in claim 1 or a pharmaceutically acceptable salt thereof.

11. Method according to claim 10 in which the domestic animal is infected with parasitic nematode worms.

12. Method according to claim 10 in which the domestic animal is infected with parasitic trematodes.

13. Method according to claim 10 in which the amount of benzene compound administered to the domestic animal is at least 1 mg./kg. animal body weight.

14. Method according to claim 10 in which the benzene compound is administered to the domestic animal in a medicated feedstuff containing between 0.001% and 3% by weight of the benzene compound.

15. Method according to claim 10 in which the domestic animals are cattle, sheep, pigs, goats, poultry or equines.

16. Therapeutic compositions which comprise, as the active ingredient, at least one benzene compound as claimed in claim 1 in association with a significant amount of a pharmaceutically acceptable carrier.

17. Medicated animal feedstuffs comprising an animal feedstuff and between 0.001% and 3% by weight of at least one benzene compound as claimed in claim 1.

18. Concentrates or supplements for addition to animal feedstuffs comprising at least one benzene compound as claimed in claim 1 in association with an inert physiologically innocuous carrier or diluent, the amount of benzene compound present being from 0.02% to 90% by weight of the composition.

19. Fungicidal compositions which comprise, as the active ingredient, at least one benzene compound as claimed in claim 1, any anion X⁻ present in the benzene compound being an agriculturally acceptable anion, in association with one or more diluents compatible with the benzene compound and suitable for use in agricultural fungicidal compositions, the amount of benzene compound present in the composition being between 0.005% and 95% by weight of the composition.

20. Method for the destruction of fungi pathogenic to plants which comprises the application of a fungicidal composition as claimed in claim 19 to a crop-growing area infested with said fungi.

21. Method according to claim 20 in which the fungicidal composition is applied to a crop-growing area at a rate of from 0.25 to 3 lbs. of benzene compound per acre.

22. Method for the protection of seeds against fungi which comprises the treatment of the seeds with a fungicidal composition as claimed in claim 19, the amount of benzene compound applied to the seeds being from 0.05% to 0.2% by weight of the seeds being treated.

23. Method for the protection from fungi of fruits after harvest which comprises the treatment of the fruits with a fungicidal composition as claimed in claim 19.

24. Method according to claim 23 in which the fruit is treated with an aqueous composition containing 0.25 to 3 lbs. of benzene compound per 100 gallons of water.

25. A benzene derivative according to claim 1 which is 4-(2-ethylthioethylthio)-1-(3-methoxycarbonyl-2-thioureido)-2-(2-dimethylaminoacetamido)benzene or 4[2-(ethylthio)ethoxy]-1-(3-methoxycarbonyl-2-thioureido)-2-(2-dimethylaminoacetamido)benzene, or a salt of a said benzene derivative having present a pharmaceutically acceptable or agriculturally acceptable anion.

26. A benzene derivative of the formula:

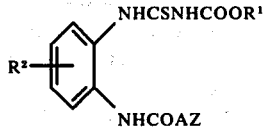

wherein R¹ represents alkyl of 1 to 4 carbon atoms, R² represents a group selected from —SR³, —SOR³, —SO₂R³, and —OR³, wherein R³ represents alkyl of 1 to 6 carbon atoms, cycloalkyl of 3 to 7 carbon atoms, alkenyl or alkynyl of 3 to 6 carbon atoms, aralkyl with 1 or 2 carbon atoms in the alkyl moiety, or R³ represents an aryl group or an aryl group substituted by a halogen atom or an alkyl or alkoxy group of 1 to 3 carbon atoms, or represents cycloalkylalkyl in which the cycloalkyl moiety contains from 3 to 7 carbon atoms and the alkyl moiety contains 1 or 2 carbon atoms, the position of R² on the benzene ring being either para to the group -NHCSNHCOOR¹ or para to the group -NHCOAZ, A represents a bivalent straight-chain aliphatic hydrocarbon radical of 1 to 4 carbon atoms or a said hydrocarbon radical substituted by at least one methyl group, and Z represents a group of the formula:

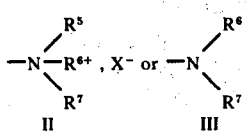

wherein R⁵ represents hydrogen or alkyl of 1 to 4 carbon atoms, R⁶ represents hydrogen, alkyl of 1 to 4 carbon atoms, or phenylalkyl with 1 or 2 carbon atoms in the alkyl moiety, and R⁷ represents hydrogen or alkyl of 1 to 4 carbon atoms, and X⁻ represents a pharmaceutically acceptable or agriculturally acceptable anion.

27. A benzene derivative according to claim 26 which is 4-(3-methoxycarbonyl-2-thioureido)-3-(2-dimethyl-aminoacetamido)diphenyl thioether, or a salt thereof having present a pharmaceutically acceptable or agriculturally acceptable anion.

28. A benzene derivative according to claim 26 which is 4-(3-methoxycarbonyl-2-thioureido)-3-(2-trimethylammonioacetylamino)diphenyl thioether iodide.

29. A benzene derivative according to claim 26 wherein R³ represents alkyl of 1 to 6 carbon atoms, cycloalkyl of 3 to 7 carbon atoms, alkenyl or alkynyl of 3 to 6 carbon atoms, aralkyl with 1 or 2 carbon atoms in the alkyl moiety, or an aryl group.

30. A benzene derivative according to claim 26 wherein Z represents a group of formula II as depicted in claim 28 and X⁻ represents a pharmaceutically acceptable anion.

31. A benzene derivative according to claim 30 wherein X⁻ represents a chloride or methanesulphonate ion.

32. A benzene derivative according to claim 26 wherein R¹ represents methyl, R² represents a group selected from —SR³, —SOR³ and -OR³, wherein R³ is alkyl of 2 to 4 carbon atoms, cycloalkyl of 3 to 7 carbon atoms, benzyl or phenyl, A represents methylene, ethylene or ethylidene and Z represents a group of formula II or III as depicted in Claim 28 wherein R⁶ and R⁷ represents hydrogen, alkyl of 1 to 3 carbon atoms, and in formula II when present, R⁵ represents hydrogen an X⁻ represents a halide ion or a methanesulphonate ion.

33. A benzene derivative according to claim 26 wherein R¹ represents methyl, R² represents phenylthio or cyclopentylthio, A represents methylene, ethylene or ethylidene, and Z represents a group of formula II or III as depicted in Claim 28 wherein R⁶ and R⁷ each represent methyl, and, in formula II (when present), R⁵ represent hydrogen and X⁻ represents a chloride or methanesulphonate ion.

34. A benzene derivative according to claim 26 wherein R¹ represents methyl or ethyl, R² represents phenylthio and Z represents a group of formula II as depicted in claim 28 wherein R⁵, R⁶ and R⁷ each represent hydrogen or methyl and X⁻ represents a halide ion or methanesulphonate ion, or Z represents a group of formula III wherein R⁶ and R⁷ each represent hydrogen or methyl.

35. A benzene derivative according to claim 32 wherein X⁻ represents a chloride ion.

36. A benzene derivative according to claim 34 wherein X⁻ represents a chloride ion.

37. A benzene derivative according to claim 26 which is 3-(3-methoxycarbonyl-2-thioureido)-4-(2-dimethylaminoacetamido)diphenyl thioether, 4'-chloro-3-(3-methoxycarbonyl-2-thioureido)-4-(2-dimethylaminoacetamido)-diphenyl thioether, 3-(3-methoxycarbonyl-2-thioureido)-4'-methyl-4-(2-dimethylaminoacetamido)diphenyl thioether, 4-(3-methoxycarbonyl-2-thioureido)-3-(2-dimethylaminoacetamido)diphenyl ether, 1-(3-methoxycarbonyl-2-thioureido)-2-(2-dimethylaminoacetamido)-4-methoxycarbonyl-2-thioureido)-2-(2-dimethylaminoacetamido)benzene, 4-ethylthio-1-(3-methoxycarbonyl-2-thioureido)-2-(2-dimethylaminoacetamido)-benzene, 4-benzylthio-1-(3-methoxycarbonyl-2-thioureido)-2-(2-dimethylaminoacetamido)benzene, 4-n-butylthio-1-(3-methoxycarbonyl-2-thioureido)-2-(2-dimethylaminoacetamido)benzene, 4-cyclopentylthio-1-(3-methoxycarbonyl-2-thioureido)-2-(2-dimethylaminoacetamido)benzene, 4-(3-methoxycarbonyl-2-thioureido)-3-(2-dimethylaminoacetamido)diphenyl sulphoxide, 4-(3-methoxycarbonyl-2-thioureido)-3-(3-dimethylaminopropionamido)diphenyl thioether, 3-(2-diethylaminoacetamido)-4-(3-methoxycarbonyl-2-thioureido)diphenyl thioether, 4-(3-methoxycarbonyl-2-thioureido)-3-(2-dimethylaminoacetamido)diphenyl ether 3-(2-diethylaminoacetamido)-4-(3-methoxycarbonyl-2-thioureido)-diphenyl ether, 4-(3-methoxycarbonyl-2-thioureido)-3-(2-dimethylaminopropionamido)diphenyl thioether, 4-(2-aminoacetamido)-3-(3-methoxycarbonyl-2-thioureido)diphenyl thioether, 4-(2-aminoacetamido)-3-(3-ethoxycarbonyl-2-thioureido)-diphenyl thioether, 3-(3-methoxycarbonyl-2-thioureido)-4-[2-(N-methylamino)acetamido]-diphenyl thioether, 3-(2-aminoacetamido)-4-(3-methoxycarbonyl-2-thioureido)-diphenyl thioether, 4-(2-aminoacetamido)-3-(3-methoxycarbonyl-2-thioureido)-4'-methyl-diphenyl thioether, 3-(2-aminoacetamido)-4-(3-methoxycarbonyl-2-thioureido)-diphenyl ether, 4-(2-aminoacetamido)-4'-chloro-3-(3-methoxycarbonyl-2-thioureido)diphenyl thioether, 3-(2-dimethylaminoacetamido)-4-[3-(2-methylpropoxycarbonyl)-2-thioureido]diphenyl thioether, 4-(3-n-butoxycarbonyl-2-thioureido)-3-(2-dimethyl-aminoacetamido)diphenyl thioether, or 4-(3-methoxycarbonyl-2-thioureido)-3-(2-di-n-propylaminoacetamido)diphenyl thioether, or a salt of a benzene derivative having present a pharmaceutically acceptable or agriculturally acceptable anion.

38. Method for the treatment of helminth infections in man and domestic animals which comprises administering to man or a domestic animal infected with helminths an anthelmintically effective amount of at least one benzene derivative as claimed in claim 26 or a pharmaceutically acceptable salt thereof.

39. Method according to claim 38 in which the domestic animal is infected with parasitic nematode worms.

40. Method according to claim 38 in which the domestic animal is infected with parasitic trematodes.

41. Method according to claim 38 in which the amount of benzene compound administered to the domestic animal is at least 1 mg/kg animal body weight.

42. Method according to claim 38 in which the benzene compound is administered to the domestic animal in a medicated feedstuff containing between 0.001% and 3% by weight of the benzene compound.

43. Method according to claim 38 in which the domestic animals are cattle, sheep, pigs, goats, poultry or equines.

44. Therapeutic compositions which comprise, as the active ingredient, at least one benzene compound as claimed in Claim 26 in association with a significant amount of a pharmaceutically acceptable carrier.

45. Medicated animal feedstuffs comprising an animal feedstuff and between 0.001% and 3% by weight of at least one benzene compound as claimed in claim 26.

46. Concentrates or supplements for addition to animal feedstuffs comprising at least one benzene compound as claimed in claim 26 in association with an inert physiologically innocuous carrier or diluent, the amount of benzene compound present being from 0.02% to 90% by weight of the composition.

47. Fungicidal compositions which comprise, as the active ingredient, at least one benzene compound as claimed in Claim 26, any anion $X^-$ present in the benzene compound being an agriculturally acceptable anion, in association with one or more diluents compatible with the benzene compound and suitable for use in agricultural fungicidal compositions, the amount of benzene compound present in the cmposition being between 0.005% and 95% by weight of the composition.

48. Method for the destruction of fungi pathogenic to plants which comprises the application of a fungicidal composition as claimed in claim 47 to a crop-growing area infested with said fungi.

49. Method according to claim 48 in which the fungicidal compositon is applied to a crop-growing area at a rate of from 0.25 to 3 lbs. of benzene compound per acre.

50. Method for the protection of seeds against fungi which comprises the treatment of the seeds with a fungicidal composition as claimed in claim 47, the amount of benzene compound applied to the seeds being from 0.05% to 0.2% by weight of the seeds being treated.

51. Method for the protection from fungi of fruits after harvest which comprises the treatment of the fruits with a fungicidal composition as claimed in claim 47.

52. Method according to claim 51 in which the fruit is treated with an aqueous composition containing 0.25 to 3 lbs. of benzene compound per 100 gallons of water.

53. A benzene derivative according to claim 26 which is 2-(3-ethoxycarbonyl-2-thioureido)-1-(2-dimethylaminoacetamido)-4-methylsulphonylbenzene.

* * * * *